(12) United States Patent
McNally

(10) Patent No.: US 9,499,817 B2
(45) Date of Patent: Nov. 22, 2016

(54) ANTISENSE POLYNUCLEOTIDES TO INDUCE EXON SKIPPING AND METHODS OF TREATING DYSTROPHIES

(71) Applicant: Elizabeth McNally, Oak Park, IL (US)

(72) Inventor: Elizabeth McNally, Oak Park, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 0 days.

(21) Appl. No.: 14/426,348

(22) PCT Filed: Sep. 6, 2013

(86) PCT No.: PCT/US2013/058636
§ 371 (c)(1),
(2) Date: Mar. 5, 2015

(87) PCT Pub. No.: WO2014/039916
PCT Pub. Date: Mar. 13, 2014

(65) Prior Publication Data
US 2015/0225718 A1 Aug. 13, 2015

Related U.S. Application Data

(60) Provisional application No. 61/697,766, filed on Sep. 6, 2012.

(51) Int. Cl.
*C12N 15/11* (2006.01)
*A61K 48/00* (2006.01)
(Continued)

(52) U.S. Cl.
CPC ....... *C12N 15/113* (2013.01); *A61K 47/48215* (2013.01); *C12N 15/1138* (2013.01); *C12N15/111* (2013.01); *C12N 2310/11* (2013.01); *C12N 2310/351* (2013.01); *C12N 2310/3535* (2013.01); *C12N 2320/30* (2013.01); *C12N 2320/33* (2013.01)

(58) Field of Classification Search
USPC .......................................... 514/44; 536/24.5
See application file for complete search history.

(56) References Cited

U.S. PATENT DOCUMENTS

3,687,808 A 8/1972 Merigan et al.
4,845,205 A 7/1989 Huynh Dinh et al.
(Continued)

FOREIGN PATENT DOCUMENTS

EP 1072679 A2 1/2001
WO WO-97/12896 4/1997
(Continued)

OTHER PUBLICATIONS

Aartsma-Rus et al,. Overview on DMD exon skipping, *Methods Mol Biol.*, 867:97-116 (2012).
(Continued)

*Primary Examiner* — Terra C Gibbs
(74) *Attorney, Agent, or Firm* — Marshall, Gerstein & Borun LLP

(57) ABSTRACT

Antisense polynucleotides and their use in pharmaceutical compositions to induce exon skipping in targeted exons of the gamma sarcoglycan gene are provided, along with methods of preventing or treating dystrophic diseases such as Limb-Girdle Muscular Dystrophy. One aspect the disclosure provides an isolated antisense polynucleotide wherein the polynucleotide specifically hybridizes to an exon target region of a gamma sarcoglycan RNA, wherein the exon is selected from the group consisting of exon 4 (SEQ ID NO:1), exon 5 (SEQ ID NO: 2), exon 6 (SEQ ID NO: 3), exon 7 (SEQ ID NO: 4) and a combination thereof. In some embodiments, the antisense polynucleotide cannot form an RNase H substrate, and in further embodiments the antisense polynucleotide comprises a modified polynucleotide backbone.

29 Claims, 18 Drawing Sheets

(51) Int. Cl.
  *C07H 21/02* (2006.01)
  *C07H 21/04* (2006.01)
  *C12N 15/113* (2010.01)
  *A61K 47/48* (2006.01)

(56) References Cited

U.S. PATENT DOCUMENTS

| | | | |
|---|---|---|---|
| 5,130,302 | A | 7/1992 | Spielvogel et al. |
| 5,134,066 | A | 7/1992 | Rogers et al. |
| 5,139,941 | A | 8/1992 | Muzyczka et al. |
| 5,149,797 | A | 9/1992 | Pederson et al. |
| 5,175,273 | A | 12/1992 | Bischofberger et al. |
| 5,252,479 | A | 10/1993 | Srivastava |
| 5,328,688 | A | 7/1994 | Roizman |
| 5,367,066 | A | 11/1994 | Urdea et al. |
| 5,432,272 | A | 7/1995 | Benner |
| 5,457,187 | A | 10/1995 | Gmeiner et al. |
| 5,459,255 | A | 10/1995 | Cook et al. |
| 5,474,935 | A | 12/1995 | Chatterjee et al. |
| 5,484,908 | A | 1/1996 | Froehler et al. |
| 5,502,177 | A | 3/1996 | Matteucci et al. |
| 5,525,711 | A | 6/1996 | Hawkins et al. |
| 5,539,082 | A | 7/1996 | Nielsen et al. |
| 5,552,540 | A | 9/1996 | Haralambidis |
| 5,585,362 | A | 12/1996 | Wilson et al. |
| 5,587,469 | A | 12/1996 | Cook et al. |
| 5,594,121 | A | 1/1997 | Froehler et al. |
| 5,596,091 | A | 1/1997 | Switzer |
| 5,614,617 | A | 3/1997 | Cook et al. |
| 5,622,856 | A | 4/1997 | Natsoulis |
| 5,631,237 | A | 5/1997 | Dzau et al. |
| 5,645,985 | A | 7/1997 | Froehler et al. |
| 5,658,776 | A | 8/1997 | Flotte et al. |
| 5,661,033 | A | 8/1997 | Ho et al. |
| 5,670,488 | A | 9/1997 | Gregory et al. |
| 5,681,941 | A | 10/1997 | Cook et al. |
| 5,693,509 | A | 12/1997 | Cotten et al. |
| 5,707,618 | A | 1/1998 | Armentano et al. |
| 5,714,331 | A | 2/1998 | Buchardt et al. |
| 5,719,262 | A | 2/1998 | Buchardt et al. |
| 5,750,692 | A | 5/1998 | Cook et al. |
| 5,763,588 | A | 6/1998 | Matteucci et al. |
| 5,773,289 | A | 6/1998 | Samulski et al. |
| 5,789,390 | A | 8/1998 | Descamps et al. |
| 5,792,453 | A | 8/1998 | Hammond et al. |
| 5,824,544 | A | 10/1998 | Armentano et al. |
| 5,830,653 | A | 11/1998 | Froehler et al. |
| 5,830,727 | A | 11/1998 | Wang et al. |
| 5,834,441 | A | 11/1998 | Philip et al. |
| 5,849,571 | A | 12/1998 | Glorioso et al. |
| 5,851,521 | A | 12/1998 | Branellec et al. |
| 5,856,152 | A | 1/1999 | Wilson et al. |
| 5,863,541 | A | 1/1999 | Samulski et al. |
| 5,879,934 | A | 3/1999 | DeLuca |
| 6,005,096 | A | 12/1999 | Matteucci et al. |
| 7,223,833 | B1 | 5/2007 | Nielsen et al. |
| 2004/0005707 | A1* | 1/2004 | Cooper ............ C07H 21/04 435/375 |
| 2008/0113351 | A1 | 5/2008 | Naito et al. |

FOREIGN PATENT DOCUMENTS

| | | |
|---|---|---|
| WO | WO-98/39352 A1 | 9/1998 |
| WO | WO-99/14226 A2 | 3/1999 |
| WO | WO-2005/116204 | 12/2005 |

OTHER PUBLICATIONS

Aartsma-Rus et al., Antisense-mediated exon skipping: a versatile tool with therapeutic and research applications, *RNA*, 13:1609-24 (2007).
Aartsma-Rus et al., Overview on AON design, *Methods Mol. Biol.*, 867:117-29 (2012).
Aartsma-Rus et al., Therapeutic antisense-induced exon skipping in cultured muscle cells from six different DMD patients, *Hum. Mol. Genet.*, 12:907-14 (2003).
Aartsma-Rus et al., Therapeutic exon skipping for dysferlinopathies?, *Euro, J. Hum. Genet.*, 18:889-94 (2010).
Allikian et al., Processing and assembly of the dystrophin glycoprotein complex, *Traffic*, 8:177-83 (2007).
Allikian et al., Reduced life span with heart and muscle dysfunction in *Drosophila* sarcoglycan mutants, *Hum. Mol. Genet.*, 16:2933-43 (2007).
Ausubel et al., Current Protocols in Molecular Biology, Greene Publishing Associates and John Wiley & Sons, New York, N.Y. (1994).
Bansal et al., Defective membrane repair in dysferlin-deficient muscular dystrophy, *Nature*, 423:168-72 (2003).
Bertoni, Clinical approaches in the treatment of Duchenne muscular dystrophy (DMD) using oligonucleotides, *Front Biosci.*, 13:517-27 (2008).
Boshart et al., A very strong enhancer is located upstream of an immediate early gene of human cytomegalovirus, *Cell*, 41:521-30 (1985).
Brand et al., Targeted gene expression as a means of altering cell fates and generating dominant phenotypes, *Development*, 118:401-15 (1993).
Chan et al., Molecular organization of sarcoglycan complex in mouse myotubes in culture, *J. Cell Biol.*, 143:2033-44 (1998).
Chen et al., High-efficiency transformation of mammalian cells by plasmid DNA, *Mol. Cell Biol.*, 7:2745-52 (1987).
Chen et al., Identification of functional domains in sarcoglycans essential for their interaction and plasma membrane targeting, *Exp. Cell. Res.*, 312:1610-25 (2006).
Cirak et al., Exon skipping and dystrophin restoration in patients with Duchenne muscular dystrophy after systemic phosphorodiamidate morpholino oligomer treatment: an open-label, phase 2, dose-escalation study, *Lancet*, 378:595-605 (2011).
Cook, Anti-Cancer Drug Design, Concise Encyclopedia of Polymer Science and Engineering, John Wiley & Sons, 6:585-607 (1991).
Crosbie et al., Molecular and genetic characterization of sarcospan: insights into sarcoglycan-sarcospan interactions, *Hum. Mol. Genet.*, 9:2019-27 (2000).
Curtis et al., Morphology of the pupal heart, adult heart, and associated tissues in the fruit fly, *Drosophila melanogaster, Morphology*, 240:225 (1999).
Davis et al., Direct gene transfer into skeletal muscle in vivo: factors affecting efficiency of transfer and stability of expression, *Hum. Gene Ther.*, 4:151 (1993).
Dean, Nonviral gene transfer to skeletal, smooth, and cardiac muscle in living animals, *Am. J. Physiol. Cell. Physiol.*, 289(2):C233-45 (2005).
Deleavy et al., Chemical Modificaiton of SiRNA, *Curr. Prot. Nuc. Acid. Chem.*, 39:1-22 (2009).
Doherty et al., Normal myoblast fusion requires myoferlin, *Development*, 132:5565-75 (2005).
Doriguzzi et al., Congenital muscular dystrophy associated with familial junctional epidermolysis bullosa letalis, *Eur. Neurol.*, 33:454-60 (1993).
Dubowitz, Muscle disorders in childhood. Saunders, Philadelphia. xiii, 282 (1978).
Duclos et al., Progressive muscular dystrophy in alpha-sarcoglycan-deficient mice, *J. Cell Biol.*, 142:1461-71 (1998).
Eckstein (ed.) Oligonucleotides and Analogues, 1st Ed. Oxford University Press, New York, (1991).
Englisch et al., Chemically Modified Oligonucleotides as Probes and Inhibitors, Angewandte Chemie, International Edition, 30: 613-722 (1991).
Fechheimer et al., Transfection of mammalian cells with plasmid DNA by scrape loading and sonication loading, *Proc. Natl. Acad. Sci. USA*, 84:8463-7 (1987).
Feigner, Improvements in cationic liposomes for in vivo gene transfer, *Hum. Gene Ther.*, 7(15):1791-3 (1996).
Feigner, Nonviral strategies for Improvements for Gene Therapy, *Sci Am.*, 276(6):102-6 (1997).

(56) References Cited

OTHER PUBLICATIONS

Fraley et al., Entrapment of a bacterial plasmid in phospholipid vesicles: potential for gene transfer, *Proc. Natl. Acad. Sci. USA*, 76:3348-52 (1979).

Freier et al., The ups and downs of nucleic acid duplex stability: structure-stability studies on chemically-modified DNA:RNA duplexes, *Nucleic Acids Research*, 25:4429-43 (1997).

Gnatenko et al., Characterization of recombinant adeno-associated virus-2 as a vehicle for gene delivery and expression into vascular cells, *J. Invest. Med.*, 45:87-98 (1997).

Goldstein et al., Mechanisms of muscle weakness in muscular dystrophy, *J. Gen. Physiol.*, 136: 29-34 (2010).

Goldstein et al., SMAD signaling drives heart and muscle dysfunction in a *Drosophila* model of muscular dystrophy, *Hum. Mol. Genet.*, 20:894-904 (2011).

Gopal, Gene transfer method for transient gene expression, stable transformation, and cotransformation of suspension cell cultures, *Mol. Cell Biol.*, 5:1188-90 (1985).

Graham et al., A new technique for the assay of infectivity of human adenovirus 5 DNA, *Virology*, 52:456-67 (1973).

Hack et al., Differential requirement for individual sarcoglycans and dystrophin in the assembly and function of the dystrophin-glycoprotein complex, *J. Cell Sci.*, 113(14):2535-44 (2000).

Hack et al., Gamma-sarcoglycan deficiency leads to muscle membrane defects and apoptosis independent of dystrophin, *J. Cell Biol.*, 142:1279-87 (1998).

Harland et al., Translation of mRNA injected into Xenopus oocytes is specifically inhibited by antisense RNA, *J. Cell Biol.*, 101:1094-9 (1985).

Heydemann et al., Genetic background influences muscular dystrophy, *Neuromuscul. Disord.*, 15(9-10):601-9 (2005).

Heydemann et al., Latent TGF-beta-binding protein 4 modifies muscular dystrophy in mice, *J. Clin. Invest.*, 119(12):3703-12 (2009).

Hoffman, et al., Dystrophin: the protein product of the Duchene muscular dystrophy locus. 1987, *Biotechnology*, 24: 457-66 (1992).

Honda et al., Specific knockdown of delta-sarcoglycan gene in C2C12 in vitro causes post-translational loss of other sarcoglycans without mechanical stress, *Mol. Cell. Biochem.*, 323(12):149-59 (2009).

Isner et al., Arterial gene therapy for restenosis, *Human Gene Therapy*, 7:989-1011 (1996).

Isner et al., Arterial gene therapy for therapeutic angiogenesis in patients with peripheral artery disease, *Circulation*, 91: 2687-92 (1995).

Katz, The reverseible reaction of sodium thymonucleate and mercuric chloride, *J. Am. Chem. Soc.*, 74:2238 (1951).

Kaufman et al., Electroporation- and mechanical ventilation-mediated gene transfer to the lung, *Gene Ther.*, 17(9):1098-104 (2010).

Kendall et al., Dantrolene enhances antisense-mediated exon skipping in human and mouse models of Duchenne muscular dystrophy, *Sci. Transl. Med.*, 4(164):164 (2012).

Kim et al., Minimal requirement for a lentivirus vector based on human immunodeficiency virus type 1, *J. Virol.*, 72(1):811-6 (1998).

Kimura et al., Cell-lineage regulated myogenesis for dystrophin replacement: a novel therapeutic approach for treatment of muscular dystrophy, *Hum. Mol. Genet.*, 17:2507-17 (2008).

Kingsman, A new generation of gene therapy vectors, Scrip Magazine, Oct., 43-46 (1998).

Klein et al., High-velocity microprojectiles for delievering nucleic acids into living cells, *Nature*, 327:70-3 (1987).

Kosturko et al., The crystal and molecular structure of a 2:1 complex of 1-methylthymine-mercury (II), *Biochemistry*, 13:3949 (1974).

Kroschwitz (ed.), The Concise Encyclopedia of Polymer Science and Engineering, pp. 858-859, John Wiley & Sons, (1990).

Lasa et al., Severe limb girdle muscular dystrophy in Spanish gypsies: further evidence for a founder mutation in the gamma-sarcoglycan gene, *Eur. J. Hum. Genet.*, 6:396-9 (1998).

Lattanzi et al., High efficiency myogenic conversion of human fibroblasts by adenoviral vector-mediated MyoD gene transfer. An alternative strategy for ex vivo gene therapy of primary myopathies, *J. Clin. Invest.*, 101:2119-28 (1998).

Lehner et al., Comparative sequence analysis of human cytomegalovirus strains, *J. Clin. Microbiol.*, 29:2494-502, 1991;.

Li et al., Inhibition of desmin expression blocks myoblast fusion and interferes with the myogenic regulators MyoD and myogenin, *J. Cell Biol.*, 124:827-41 (1994).

Liu et al., RNAi-based Gene Therapy for Dominant Limb Girdle Muscular Dystrophies, *Curr. Gene Ther.*, 12(4):307-14 (2012).

Magnusson et al., Sustained, high transgene expression in liver with plasmid vectors using optimized promoter-enhancer combinations, *J. Gene Med.*, 13(7-8):382-91 (2011).

Martin, Remington's Pharmaceutical Sciences, 18th Ed., Mack Publishing Co., Easton, PA. (1990).

Matsuda et al., Visualization of dystrophic muscle fibers in mdx mouse by vital staining with Evans blue: evidence of apoptosis in dystrophin-deficient muscle, *J. Biochem.*, 118:959-64 (1995).

McNally et al., Mild and severe muscular dystrophy caused by a single gamma-sarcoglycan mutation, *Am. J. Hum. Genet.*, 59:1040-7 (1996).

McNally et al., Mutations that disrupt the carboxyl-terminus of gamma-sarcoglycan cause muscular dystrophy, *Hum. Mol. Genet.*, 5:1841-7 (1996).

Moser, Duchenne muscular dystrophy: pathogenetic aspects and genetic prevention, *Hum. Genet.*, 66:17-40 (1984).

Nicolau et al., Liposome-mediated DNA transfer in eukaryotic cells. Dependence of the transfer efficiency upon the type of liposomes used and the host cell cycle stage, *Biochim. Biophys. Acta.*, 721:185-90 (1982).

Nielsen et al., Sequence-selective recognition of DNA by strand displacement with a thymine-substituted polyamide, *Science*, 254:1497-500 (1991).

Noguchi et al., Formation of sarcoglycan complex with differentiation in cultured myocytes, *Eur. J. Biochem.*, 267:640-8 (2000).

Noguchi et al., Mutations in the dystrophin-associated protein gamma-sarcoglycan in chromosome 13 muscular dystrophy, *Science*, 270:819-22 (1995).

Ohlendieck et al., Dystrophin-glycoprotein complex is highly enriched in isolated skeletal muscle sarcolemma, *J. Cell Biol.*, 112:135-48 (1991).

Pacak et al., Tissue specific promoters improve specificity of AAV9 mediated transgene expression following intra-vascular gene delivery in neonatal mice, *Genet. Vaccines Ther.*, 6:13 (2008).

Passos-Bueno et al., Half the dystrophin gene is apparently enough for a mild clinical course: confirmation of its potential use for gene therapy, *Hum. Mol. Genet.*, 3:919-22 (1994).

Potter et al., Enhancer-dependent expression of human kappa immunoglobulin genes introduced into mouse pre-B lymphocytes by electroporation, *Proc. Nat. Acad. Sci. USA*, 81:7161-5 (1984).

Quantin et al., Adenovirus as an expression vector in muscle cells in vivo, *Proc. Natl. Acad. Sci. USA*, 89:2581-4 (1992).

Rippe et al., DNA-mediated gene transfer into adult rat hepatocytes in primary culture, *Mol. Cell Biol.*, 10:689-95 (1990).

Rosenfeld et al., In vivo transfer of the human cystic fibrosis transmembrane conductance regulator gene to the airway epithelium, *Cell*, 68:143-55 (1992).

Sambrook et al., Molecular Cloning, a Laboratory Manual, 2d edition, Cold Spring Harbor Press, Cold Spring Harbor, N.Y. (1989).

Sanghvi, Antisense Research and Application, Ed. S. T. Crooke and B. Lebleu, CRC Press, (1991).

Shcherbata et al., Dissecting muscle and neuronal disorders in a *Drosophila* model of muscular dystrophy, *EMBO J.*, 26:481-93 (2007).

Stratford-Perricaudet et al., Widespread long-term gene transfer to mouse skeletal muscles and heart, *J. Clin. Invest.*, 90:626-30 (1992).

Su et al., A gene atlas of the mouse and human protein-encoding transcriptomes, *Proc. Natl. Acad. Sci. USA*, 101:6062-7 (2004).

Swaggart et al., Distinct genetic regions modify specific muscle groups in muscular dystrophy, *Physiol. Genomics*, 43(1):24-31 (2011).

(56) References Cited

OTHER PUBLICATIONS

Thomas, Refining stability and dissolution rate of amorphous drug formulations, *J. Am. Chem. Soc.*, 76:6032 (1954).
Tur-Kaspa et al., Use of electroporation to introduce biologically active foreign genes into primary rat hepatocytes, *Mol. Cell Biol.*, 6: 716-8 (1986).
van Roon-Mom et al., Overview on applications of antisense-mediated exon skipping, *Methods Mol. Biol.*, 867:79-96 (2012).
Wang et al., Successful regional delivery and long-term expression of a dystrophin gene in canine muscular dystrophy: a preclinical model for human therapies, *Mol. Ther.*, 20(8):1501-7 (2012).
Weintraub et al., The myoD gene family: nodal point during specification of the muscle cell lineage, *Science*, 251:761-6 (1991).
Wolf et al., *Drosophila* as a model for the identification of genes causing adult human heart disease, *Proc. Natl. Acad. Sci. USA.*, 103:1394-9 (2006).
Wu et al., Liver-directed gene delivery, *Adv. Drug Delivery Rev.*, 12:159-67 (1993).
Wu et al., Evidence for targeted gene delivery to Hep G2 hepatoma cells in vitro, *Biochemistry*, 27:887-92 (1988).
Wu et al., Receptor-mediated in vitro gene transformation by a soluble DNA carrier system, *J. Biol. Chem.*, 262:4429-32 (1987).
Yamane, et al., On the complexing of desoxyribonucleic acid (DNA) by Mercuric Ion, *J. Am. Chem. Soc.*, 83:2599 (1961).
Yang et al., In vivo and in vitro gene transfer to mammalian somatic cells by particle bombardment, *Proc. Natl. Acad. Sci USA*, 87:9568-72 (1990).
Zhang et al., Dual AAV therapy ameliorates exercise-induced muscle injury and functional ischemia in murine models of Duchenne muscular dystrophy, *Hum. Mol. Genet.*, 22(18):3720-9 (2013).
Zhang, et al., An extremely stable and orthogonal DNA base pair with a simplified three-carbon backbone, *J. Am. Chem. Soc.*, 127:74-5 (2005).
Zhu et al., Cardiomyopathy is independent of skeletal muscle disease in muscular dystrophy, *FASEB J.*, 16:1096-8 (2002).
Zimmermann et al., A novel silver(i)-mediated DNA base pair, *J. Am. Chem. Soc.*, 124:13684-13685 (2002).
International Search Report and Written Opinion of the International Searching Authority, PCT/US2013/05866, dated Jan. 16, 2014.
International Preliminary Report on Patentability, PCT/US2013/05866, dated Mar. 10, 2015.
Aartsma-Rus et al., "Therapeutic exon skipping for dysferlinopathies?," European Journal of Human Genetics, 18(8):889-894 (2010).
Barton "Restoration of γ-Sarcoglycan Localization and Mechanical Signal Transduction Are Independent in Murine Skeletal Muscle," Journal of Biological Chemistry, 285(22):17263-17270 (2010).
Herson et al., "A phase I trial of adeno-associated virus serotype 1-γ-sarcoglycan gene therapy for limb girdle muscular dystrophy type 2c," Brain 135:483-492 (2012).
Sandona et al. "Sarcoglycanopathies: molecular pathogenesis and therapeutic prospects," 11(1):1-27 (2009).
Search Report from European Application No. 13835266.1 dated May 20, 2016.
Yoshida et al., "Bidirectional Signaling between Sarcoglycans and the Integrin Adhesion System in Cultured L6 Myocytes," Journal of Biological Chemistry, 273(3):1583-1590 (1998).

* cited by examiner

```
                        SEQUENCE LISTING

<160> NUMBER OF SEQ ID NOS: 8

<210> SEQ ID NO 1
<211> LENGTH: 148
<212> TYPE: DNA
<213> ORGANISM: Homo sapiens
<220> FEATURE:
<221> NAME/KEY: misc_feature
<222> LOCATION: (31)..(118)
<223> OTHER INFORMATION: Exon coding region

<400> SEQUENCE: 1
attttgcaaa ttttataaat ctctttctag gactcatctc tgcttctaca atcaacccag        60
aatgtgactg taaatgcgcg caactcagaa ggggaggtca caggcaggtt aaaagtcggt       120
gagtccagct tcatcatggt gctttgca                                          148

<210> SEQ ID NO 2
<211> LENGTH: 180
<212> TYPE: DNA
<213> ORGANISM: Homo sapiens
<220> FEATURE:
<221> NAME/KEY: misc_feature
<222> LOCATION: (31)..(150)
<223> OTHER INFORMATION: Exon coding region

<400> SEQUENCE: 2
agtttataat aaactgtttt aattcttcag gtcccaaaat ggtagaagtc cagaatcaac        60
agtttcagat caactccaac gacggcaagc cactatttac tgtagatgag aaggaagttg       120
tggttggtac agataaactt cgagtaactg gtatgtacta actcgagaaa aacacaacat       180

<210> SEQ ID NO 3
<211> LENGTH: 133
<212> TYPE: DNA
<213> ORGANISM: Homo sapiens
<220> FEATURE:
<221> NAME/KEY: misc_feature
<222> LOCATION: (31)..(103)
<223> OTHER INFORMATION: Exon coding region

<400> SEQUENCE: 3
gctcctgata catctttgtt ttttgtttag ggcctgaagg ggctctttt gaacattcag         60 tggagacacc ccttgtcaga gccgacccgt ttcaagacct taggtaagaa tttttgttca      120
aatattaaca acc                                                          133

<210> SEQ ID NO 4
<211> LENGTH: 204
<212> TYPE: DNA
<213> ORGANISM: Homo sapiens
<220> FEATURE:
<221> NAME/KEY: misc_feature
<222> LOCATION: (51)..(174)
<223> OTHER INFORMATION: Exon coding region

<400> SEQUENCE: 4
atttttaata cttttttttt tttttttgt gcttcttttc ctcatctcag attagaatcc         60
```

```
cccactcgga gtctaagcat ggatgcccca aggggtgtgc atattcaagc tcacgctggg      120
aaaattgagg cgctttctca aatggatatt cttttcata gtagtgatgg aatggtgagt       180
tcattcacag atcagcctcc tact                                              204
```

<210> SEQ ID NO 5
<211> LENGTH: 291
<212> TYPE: PRT
<213> ORGANISM: Homo sapiens
<220> FEATURE:
<221> NAME/KEY: MISC_FEATURE
<222> LOCATION: (100)..(130)
<223> OTHER INFORMATION: Exon 4
<220> FEATURE:
<221> NAME/KEY: MISC_FEATURE
<222> LOCATION: (131)..(169)
<223> OTHER INFORMATION: Exon 5
<220> FEATURE:
<221> NAME/KEY: MISC_FEATURE
<222> LOCATION: (170)..(193)
<223> OTHER INFORMATION: Exon 6
<220> FEATURE:
<221> NAME/KEY: MISC_FEATURE
<222> LOCATION: (194)..(234)
<223> OTHER INFORMATION: Exon 7

<400> SEQUENCE: 5

```
Met Val Arg Glu Gln Tyr Thr Thr Ala Thr Glu Gly Ile Cys Ile Glu
 1               5                  10                  15

Arg Pro Glu Asn Gln Tyr Val Tyr Lys Ile Gly Ile Tyr Gly Trp Arg
                20                  25                  30

Lys Arg Cys Leu Tyr Leu Phe Val Leu Leu Leu Ile Leu Val
            35                  40                  45

Val Asn Leu Ala Leu Thr Ile Trp Ile Leu Lys Val Met Trp Phe Ser
    50                  55                  60

Pro Ala Gly Met Gly His Leu Cys Val Thr Lys Asp Gly Leu Arg Leu
65                  70                  75                  80

Glu Gly Glu Ser Glu Phe Leu Phe Pro Leu Tyr Ala Lys Glu Ile His
                85                  90                  95

Ser Arg Val Asp Ser Ser Leu Leu Leu Gln Ser Thr Gln Asn Val Thr
            100                 105                 110

Val Asn Ala Arg Asn Ser Glu Gly Glu Val Thr Gly Arg Leu Lys Val
        115                 120                 125

Gly Pro Lys Met Val Glu Val Gln Asn Gln Gln Phe Gln Ile Asn Ser
    130                 135                 140

Asn Asp Gly Lys Pro Leu Phe Thr Val Asp Glu Lys Glu Val Val Val
145                 150                 155                 160

Gly Thr Asp Lys Leu Arg Val Thr Gly Pro Glu Gly Ala Leu Phe Glu
                165                 170                 175

His Ser Val Glu Thr Pro Leu Val Arg Ala Asp Pro Phe Gln Asp Leu
            180                 185                 190

Arg Leu Glu Ser Pro Thr Arg Ser Leu Ser Met Asp Ala Pro Arg Gly
        195                 200                 205

Val His Ile Gln Ala His Ala Gly Lys Ile Glu Ala Leu Ser Gln Met
    210                 215                 220

Asp Ile Leu Phe His Ser Ser Asp Gly Met Leu Val Leu Asp Ala Glu
225                 230                 235                 240

Thr Val Cys Leu Pro Lys Leu Val Gln Gly Thr Trp Gly Pro Ser Gly
                245                 250                 255
```

-continued

```
Ser Ser Gln Ser Leu Tyr Glu Ile Cys Val Cys Pro Asp Gly Lys Leu
            260                 265                 270

Tyr Leu Ser Val Ala Gly Val Ser Thr Thr Cys Gln Glu His Ser His
        275                 280                 285

Ile Cys Leu
    290

<210> SEQ ID NO 6
<211> LENGTH: 291
<212> TYPE: PRT
<213> ORGANISM: Mus musculus
<220> FEATURE:
<221> NAME/KEY: MISC_FEATURE
<222> LOCATION: (100)..(130)
<223> OTHER INFORMATION: Exon 4
<220> FEATURE:
<221> NAME/KEY: MISC_FEATURE
<222> LOCATION: (131)..(169)
<223> OTHER INFORMATION: Exon 5
<220> FEATURE:
<221> NAME/KEY: MISC_FEATURE
<222> LOCATION: (170)..(193)
<223> OTHER INFORMATION: Exon 6
<220> FEATURE:
<221> NAME/KEY: MISC_FEATURE
<222> LOCATION: (194)..(234)
<223> OTHER INFORMATION: Exon 7

<400> SEQUENCE: 6

Met Val Arg Glu Gln Tyr Thr Thr Val Thr Glu Gly Thr His Ile Glu
1               5                   10                  15

Arg Pro Glu Asn Gln His Ile Tyr Lys Ile Gly Ile Tyr Gly Trp Arg
            20                  25                  30

Lys Arg Cys Leu Tyr Leu Phe Val Leu Leu Leu Ala Ile Leu Val
        35                  40                  45

Val Asn Leu Ala Leu Thr Ile Trp Ile Leu Lys Val Met Trp Phe Ser
    50                  55                  60

Pro Ile Gly Met Gly His Leu His Val Thr Ala Asp Gly Leu Arg Leu
65                  70                  75                  80

Glu Gly Glu Ser Glu Phe Leu Phe Pro Leu Tyr Ala Lys Glu Ile Arg
                85                  90                  95

Ser Arg Val Asp Ser Ser Leu Leu Gln Ser Thr Gln Asn Val Thr
            100                 105                 110

Val Ser Ala Arg Asn Ser Glu Gly Glu Val Thr Gly Arg Val Lys Val
        115                 120                 125

Gly Ala Gln Met Val Glu Val Gln Ser Gln His Phe Gln Ile Asn Ser
    130                 135                 140

Glu Asp Gly Lys Pro Leu Phe Ser Ala Glu Gln Asp Val Val
145                 150                 155                 160

Gly Thr Gly Arg Leu Arg Val Thr Gly Pro Glu Gly Ala Leu Phe Glu
                165                 170                 175

His Ser Val Glu Thr Pro Leu Val Arg Ala Asp Pro Phe Gln Asp Leu
            180                 185                 190

Arg Leu Glu Ser Pro Thr Arg Ser Leu Ser Met Asp Ala Pro Arg Gly
        195                 200                 205

Val His Val Lys Ala Asn Ala Gly Lys Leu Glu Ala Leu Ser Gln Met
    210                 215                 220

Asp Ile Ile Leu Gln Ser Ser Glu Gly Val Leu Val Leu Asp Ala Glu
225                 230                 235                 240

Thr Val Gly Leu Thr Lys Leu Lys Gln Gly Thr Gln Gly Pro Ala Gly
```

```
            245                 250                 255
Ser Ser Asn Gly Phe Tyr Glu Ile Cys Ala Cys Pro Asp Gly Lys Leu
        260                 265                 270

Tyr Leu Ser Met Ala Gly Glu Val Thr Thr Cys Glu Glu His Ser His
    275                 280                 285

Val Cys Leu
    290

<210> SEQ ID NO 7
<211> LENGTH: 156
<212> TYPE: PRT
<213> ORGANISM: Homo sapiens

<400> SEQUENCE: 7

Met Val Arg Glu Gln Tyr Thr Thr Ala Thr Glu Gly Ile Cys Ile Glu
1               5                   10                  15

Arg Pro Glu Asn Gln Tyr Val Tyr Lys Ile Gly Ile Tyr Gly Trp Arg
            20                  25                  30

Lys Arg Cys Leu Tyr Leu Phe Val Leu Leu Leu Ile Ile Leu Val
        35                  40                  45

Val Asn Leu Ala Leu Thr Ile Trp Ile Leu Lys Val Met Trp Phe Ser
    50                  55                  60

Pro Ala Gly Met Gly His Leu Cys Val Thr Lys Asp Gly Leu Arg Leu
65                  70                  75                  80

Glu Gly Glu Ser Glu Phe Leu Phe Pro Leu Tyr Ala Lys Glu Ile His
                85                  90                  95

Ser Arg Val Leu Val Leu Asp Ala Glu Thr Val Cys Leu Pro Lys Leu
            100                 105                 110

Val Gln Gly Thr Trp Gly Pro Ser Gly Ser Ser Gln Ser Leu Tyr Glu
        115                 120                 125

Ile Cys Val Cys Pro Asp Gly Lys Leu Tyr Leu Ser Val Ala Gly Val
    130                 135                 140

Ser Thr Thr Cys Gln Glu His Ser His Ile Cys Leu
145                 150                 155

<210> SEQ ID NO 8
<211> LENGTH: 156
<212> TYPE: PRT
<213> ORGANISM: Mus musculus

<400> SEQUENCE: 8

Met Val Arg Glu Gln Tyr Thr Thr Ala Thr Glu Gly Ile Cys Ile Glu
1               5                   10                  15

Arg Pro Glu Asn Gln Tyr Val Tyr Lys Ile Gly Ile Tyr Gly Trp Arg
            20                  25                  30

Lys Arg Cys Leu Tyr Leu Phe Val Leu Leu Leu Ile Ile Leu Val
        35                  40                  45

Val Asn Leu Ala Leu Thr Ile Trp Ile Leu Lys Val Met Trp Phe Ser
    50                  55                  60

Pro Ala Gly Met Gly His Leu Cys Val Thr Lys Asp Gly Leu Arg Leu
65                  70                  75                  80

Glu Gly Glu Ser Glu Phe Leu Phe Pro Leu Tyr Ala Lys Glu Ile His
                85                  90                  95

Ser Arg Val Leu Val Leu Asp Ala Glu Thr Val Cys Leu Pro Lys Leu
            100                 105                 110

Val Gln Gly Thr Trp Gly Pro Ser Gly Ser Ser Gln Ser Leu Tyr Glu
```

```
             115                 120                 125
Ile Cys Val Cys Pro Asp Gly Lys Leu Tyr Leu Ser Val Ala Gly Val
    130                 135                 140

Ser Thr Thr Cys Gln Glu His Ser His Ile Cys Leu
145                 150                 155
```

ANTISENSE POLYNUCLEOTIDES TO INDUCE EXON SKIPPING AND METHODS OF TREATING DYSTROPHIES

CROSS REFERENCE TO RELATED APPLICATIONS

This application is a U.S. National Phase of PCT/US2013/058636, filed Sep. 6, 2013, which claims the priority benefit under 35 U.S.C. §119(e) of Provisional U.S. Patent Application No. 61/697,766, filed Sep. 6, 2012, the disclosures of which are incorporated herein by reference in their entirety.

STATEMENT OF GOVERNMENT INTEREST

This invention was made with government support under Grant Number HL061322 and U54AR052646 awarded by the National Institutes of Health. The government has certain rights in the invention.

FIELD OF THE INVENTION

The present disclosure relates to antisense polynucleotides and their use in pharmaceutical compositions to induce exon skipping in targeted exons of the gamma sarcoglycan gene (SGCG), useful in treating various forms of Muscular Dystrophy.

BACKGROUND OF THE INVENTION

Muscular Dystrophy (MD) is a group of more than 30 genetic disorders characterized by skeletal muscle weakness and degeneration. Limb-girdle Muscular Dystrophy (LGMD) is an autosomal class of MD. The most severely affected muscles in LGMD are those of limbs, including arms and legs, as well as the trunk muscles affecting posture and breathing. MD patients are born with normal muscle function but develop heart failure and breathing problems due to the loss of mass and strength of cardiac and respiratory muscle. Limb Girdle Muscular Dystrophy type 2C (LGMD2C) is caused by mutations in the γ-sarcoglycan (Sgcg) gene [Noguchi et al., Science 270: 819-822 (1995); McNally et al., Am J Hum Genet 59: 1040-1047 (1996); Lasa et al., Eur J Hum Genet 6: 396-399 (1998)]. γ-sarcoglycan is a dystrophin-associated protein [Allikian et al., Traffic 8: 177-183 (2007)]. Dystrophin is a large rod-shaped cytoplasmic protein found along the inner surface of the plasma membrane of muscle cells. Dystrophin is encoded by the DMD gene, which is the largest gene known so far, spanning 2.4 MB on the X chromosome [Hoffman, et al., Biotechnology 24: 457-466 (1992)]. Mutations in the DMD gene are the most common cause of muscular dystrophy, affecting 1 in every 3500 newborn boys worldwide [Moser, Hum Genet 66: 17-40 (1984)].

The dystrophin complex localizes at the muscle membrane, known as the sarcolemma, and connects intracellular actin bundles to the extracellular matrix. The dystrophin complex plays a critical role in stabilizing the sarcolemma during muscle contraction. Mutation or loss of dystrophin or the associated sarcoglycans leads to destabilization of the sarcolemma and subsequent events, such as muscle cell injury, muscle cell necrosis and fibrotic or fatty tissue deposition.

Mice and humans have a highly conserved dystrophin complex. The Sgcg null mouse model (Sgcg$^{-/-}$) was the first model established for LGMD by deleting exon 2 of Sgcg, resulting in a null allele [Hack et al., J Cell Biol 142: 1279-1287 (1998)]. γ-sarcoglycan mutant mice develop progressive disease pathology that resembles that of LGMD2C patients. Sgcg$^{-/-}$ mice are born in the expected Mendelian ratios. By 20 weeks of age, however, half of the Sgcg$^{-/-}$ mice die and the surviving mice weigh significantly less than wild-type littermates. Dystrophic changes of skeletal muscle, such as broad variation in fiber size, immune cell infiltration and fibrotic and fatty tissue deposition, are evident by 3 weeks of age but become prominent around 8 weeks of age. Consistent with the disease progression pattern in patients, cardiomyopathy in Sgcg$^{-/-}$ also develops at later stage. At 20 weeks of age, Sgcg$^{-/-}$ hearts display remarkable fibrosis and reduced cardiac function.

Disruption of the dystrophin complex makes the muscle membrane more fragile and more susceptible to membrane tears when subject to the shearing force during contraction. As a result of these tears, dystrophin or sarcoglycan null skeletal muscles show increased permeability that allows soluble enzymes such as creatine kinase to exit from the cell and blood proteins such as albumin or ions such as calcium to enter the cell. Initially, the membrane repairing machinery, including dysferlin family proteins, is activated to reseal the damaged membrane [Bansal Nature 423: 168-172 (2003); Doherty et al., Development 132: 5565-5575 (2005)]. However, this blurring of cell-environment boundary and increased cytoplasmic calcium content are associated with a series of harmful cellular events, such as increased reactive oxygen species, activation of protease cascade, and eventually lead to necrotic cell death [Goldstein et al., J Gen Physiol 136: 29-34 (2010)].

Loss of muscle fibers also activates muscle stem cells, called satellite cells. Satellite cells divide and attempt to repair injured muscle fibers. As myoblasts only have limited dividing potential, the degeneration trend gradually overcomes the regeneration efforts, resulting in irreversible muscle loss. The loss of muscle bulk is accompanied by replacement of connective and fatty tissue. Like humans, mutant mice also develop cardiomyopathy as a result of loss of cardiomyocytes and fibrotic tissue deposition. Hearts with cardiomyopathy fail to pump properly, which results in a failure to deliver oxygen and nutrients to the tissue.

*Drosophila* has a simplified dystrophin complex that shows conservation with mammals. *Drosophila* γ/δ-sarcoglycan (Sgcd) is equally similar to mammalian γ-sarcoglycan and δ-sarcoglycan. Previous work resulted in the generation of a fly model of muscular dystrophy by inducing a large deletion in the Sgcd locus via imprecise P-element excision [Allikian et al., Hum Mol Genet 16: 2933-2943 (2007)]. The Sgcd$^{840}$ line was selected and further characterized because it had a defined deletion that ablates expression of the single γ/δ-sarcoglycan gene. Similar to the progressive nature of MD in mammals, Sgcd mutant flies are normal when they emerge as adults, but develop heart and skeletal muscle abnormalities over time. Unlike the four-chamber heart in mammals, flies have a simple heart tube to promote the blood circulation. Compared to wild-type flies, heart tubes in Sgcd mutant flies are enlarged and defective in contraction. Weakness in skeletal muscle manifests in the impaired climbing ability of the mutant flies. Histological examination of flight muscle in mutant flies also revealed muscle fiber detachment from the exoskeleton, which is only infrequently seen in wild-type flies.

The most common causes of muscular dystrophy are mutations in the dystrophin gene. Different mutations in dystrophin lead to different severities. For example, a mutation which shifts the reading frame, such as the deletion of exon 43 to exon 48 [Doriguzzi et al., Eur Neurol 33: 454-460

(1993)], leads to a much more severe disease than one with a larger deletion spanning exon 13 to 48 [Passos-Bueno et al., Hum Mol Genet 3: 919-922 (1994)]. The frame shift in the former case results in loss of the C-terminus of dystrophin, which is responsible for normal localization of sarcoglycans and other dystrophin-associated proteins. Furthermore, the level of dystrophin protein is also greatly reduced, possibly due to nonsense-mediated decay or improper protein folding and subsequent degradation. In the latter case, the large deletion reduces the number of spectrin repeats in the middle region of the protein, while keeping the crucial C-terminus and N-terminus intact. This suggests that internally truncated protein can be partially functional. These milder mutations are known as forms of Becker Muscular Dystrophy (BMD).

Most eukaryotic genes are made of protein-coding exons and non-coding introns. Splicing is required to connect exons to form mature mRNA. To achieve a proper splicing pattern, recognition of splice donor, splice acceptor and exonic splicing enhancer (ESE) sites by the splicing machinery are required. Blocking essential splice sites by antisense polynucleotides (AONs) induces exclusion of certain exons from the mature mRNA [Aartsma-Rus et al., RNA 13: 1609-1624 (2007)]. This event is referred to as exon skipping.

Phase I and phase II clinic trials of therapeutic exon skipping have been carried out, proving the safety of AON administration and efficiency of dystrophin restoration [Bertoni, Front Biosci 13: 517-527 (2008); Cirak et al., Lancet 378: 595-605 (2011)]. In the phase II trial, 19 patients aged from 5-15 participated in the study. They were divided into multiple groups that received escalated doses of AVI-4568 (the AON drug) via weekly intravenous infusion for 12 weeks. No serious drug-related adverse effect was observed. Targeted exon skipping was observed in all patients and new dystrophin production was detected in a dose dependent manner. The 3 patients with greatest response to the drug had 15%, 21% and 55% dystrophin positive fibers. Consistent with the reproduction of functional dystrophin, dystrophin-associated proteins were also found restored at the plasma membrane of muscle cells.

SUMMARY OF THE INVENTION

The disclosure is directed to one or more antisense polynucleotides and their use in pharmaceutical compositions in a strategy to induce exon skipping in the gamma sarcoglycan gene in patients suffering from Limb-girdle Muscular Dystrophy-2C (i.e., LGMD2C) or in patients at risk of such a disease. The disclosure also provides methods of preventing or treating muscular dystrophy, e.g., LGMD2C, by exon skipping in the gamma sarcoglycan gene using antisense polynucleotides.

One aspect the disclosure provides an isolated antisense polynucleotide wherein the polynucleotide specifically hybridizes to an exon target region of a gamma sarcoglycan RNA, wherein the exon is selected from the group consisting of exon 4 (SEQ ID NO: 1), exon 5 (SEQ ID NO: 2), exon 6 (SEQ ID NO: 3), exon 7 (SEQ ID NO: 4) and a combination thereof. In some embodiments, the antisense polynucleotide cannot form an RNase H substrate, and in further embodiments the antisense polynucleotide comprises a modified polynucleotide backbone. In some embodiments, the modified backbone is a 2'-O-methyl-oligoribonucleotide.

TABLE 1

Gamma sarcoglycan exon sequences.

| Exon (SEQ ID NO) | Sequence (5'-3') |
|---|---|
| 4 (SEQ ID NO: 1) | ATTTTGCAAATTTTATAAATCTCTTTCTAG GACTCATCTCTGCTTCTACAATCAACCCAG AATGTGACTGTAAATGCGCGCAACTCAGAA GGGGAGGTCACAGGCAGGTTAAAAGTCGGT GAGTCCAGCTTCATCATGGTGCTTTGCA |
| 5 (SEQ ID NO: 2) | AGTTTATAATAAACTGTTTTAATTCTTCAG GTCCCAAAATGGTAGAAGTCCAGAATCAAC AGTTTCAGATCAACTCCAACGACGGCAAGC CACTATTTACTGTAGATGAGAAGGAAGTTG TGGTTGGTACAGATAAACTTCGAGTAACTG GTATGTACTAACTCGAGAAAAACACAACAT |
| 6 (SEQ ID NO: 3) | GCTCCTGATACATCTTTGTTTTTGTTTAG GGCCTGAAGGGGCTCTTTTTGAACATTCAG TGGAGACACCCCTTGTCAGAGCCGACCCGT TTCAAGACCTTAGGTAAGAATTTTTGTTCA AATATTAACAACC |
| 7 (SEQ ID NO: 4) | ATTTTTAATACTTTTTTTTTTTTTTTTTGT GCTTCTTTTCCTCATCTCAGATTAGAATCC CCCACTCGGAGTCTAAGCATGGATGCCCCA AGGGGTGTGCATATTCAAGCTCACGCTGGG AAAATTGAGGCGCTTTCTCAAATGGATATT CTTTTTCATAGTAGTGATGGAATGGTGAGT TCATTCACAGATCAGCCTCCTACT |

Underlining indicates coding region of exon. Antisense polynucleotides are contemplated to be
sequences that target an exon or an intron-exon boundary.

In further embodiments, the disclosure contemplates that the modified polynucleotide backbone comprises a modified moiety substituted for at least one sugar of at least one of the polynucleotides. In a specific embodiment, the modified moiety is a Morpholino.

It is additionally contemplated by the disclosure that, in some embodiments, the modified polynucleotide backbone of the polynucleotide comprises at least one modified internucleotide linkage, and in some embodiments the modified internucleotide linkage comprises a modified phosphate. The modified phosphate, in various embodiments, is selected from the group consisting of a methyl phosphonate, a methyl phosphorothioate, a phosphoromorpholidate, a phosphoropiperazidate and a phosphoroamidate.

The disclosure also provides embodiments wherein the polynucleotide comprises a peptide nucleic acid.

In still further embodiments, it is contemplated that the polynucleotide is chemically linked to one or more conjugates that enhance the activity, cellular distribution, or cellular uptake of the antisense polynucleotide. In related embodiments, the conjugate is a peptide that enhances cellular uptake, and in further embodiments the peptide is selected from the group consisting of a nuclear localization signal (NLS), HIV-1 TAT protein, a peptide comprising an integrin binding domain, an oligolysine, an adenovirus fiber protein and a peptide comprising a receptor-mediated endocytosis (RME) domain.

In some embodiments, the polynucleotide is chemically linked to a polyethylene glycol molecule.

In another aspect of the disclosure, a pharmaceutical composition is provided comprising the antisense polynucleotide as described herein and a physiologically compatible phosphate buffer. In some embodiments, the pharmaceutical composition further comprises an additional antisense polynucleotide, wherein the additional polynucleotide specifically hybridizes to an exon of a gamma sarcoglycan nucleic acid.

A further aspect of the disclosure provides a method of inducing exon-skipping of a gamma sarcoglycan RNA, comprising delivering to a cell a therapeutically effective or prophylactically effective amount of the antisense polynucleotide or a composition of the disclosure, thereby inducing exon-skipping of the gamma sarcoglycan RNA.

In some embodiments, the cell is a human muscle cell and in further embodiments the human muscle cell is in a patient. The patient, in various embodiments, is a patient that has muscular dystrophy. In further embodiments, the muscular dystrophy is Limb Girdle Muscular Dystrophy type 2C (LGMD2C).

In still another aspect of the disclosure, a method of ameliorating Limb Girdle Muscular Dystrophy type 2C (LGMD2C) in a patient in need thereof is provided, comprising the step of administering to the patient a therapeutically effective amount of a composition of the disclosure, thereby ameliorating LGMD2C.

The disclosure also provides a method of inhibiting the progression of dystrophic pathology associated with LGMD2C in a patient in need thereof comprising the step of administering to the patient a therapeutically effective amount of a composition of the disclosure, thereby inhibiting the progression of dystrophic pathology.

In some aspects, the disclosure provides a method of improving muscle function in a patient suffering from Limb Girdle Muscular Dystrophy type 2C (LGMD2C) comprising the step of administering to the patient a therapeutically effective amount of a composition of the disclosure, thereby improving muscle function. In some embodiments, the improvement is a cardiac muscle improvement, and in further embodiments the improvement in muscle function is an improvement in muscle strength. In further embodiments, the improvement in muscle strength is an improvement in respiratory muscle strength, and in additional embodiments the improvement in muscle function is an improvement in motor stability. In any of the embodiments of the disclosure, the improvement in respiratory muscle strength is measured as reduced nocturnal desaturation events or improved pulmonary function testing. In any of the embodiments of the disclosure, the improvement in motor stability results in an improved time to standing or climbing stairs relative to previously measured time to standing or climbing stairs.

The improvement in motor stability, in some embodiments, results in an improved six-minute walk test by the patient relative to a previously measured six-minute walk test by that patient. Additional improvements contemplated by the disclosure are assessed via improved histopathology or improved noninvasive imaging evidence such as reduced fibrofatty infiltration and reduced evidence of scarring. Cardiac muscle improvement as documented by improved left and right ventricular function, reduced right and left ventricular diameters and reduced evidence of cardiac damage is also contemplated.

Another aspect of the disclosure is drawn to a kit comprising the antisense polynucleotides as described herein, optionally in a container, and a package insert, package label, instructions or other labeling. In some embodiments, the kit further comprises an additional polynucleotide, wherein the additional polynucleotide specifically hybridizes to an exon in a gamma sarcoglycan RNA.

Additional aspects and embodiments of the disclosure are described in the following enumerated paragraphs.

1. An isolated polynucleotide encoding a mini-gamma sarcoglycan protein comprising a deletion of an exon selected from the group consisting of exon 4 (SEQ ID NO: 1), exon 5 (SEQ ID NO: 2), exon 6 (SEQ ID NO: 3), exon 7 (SEQ ID NO: 4) and a combination thereof.

2. A composition comprising a viral vector comprising the polynucleotide according to paragraph 1.

3. The composition of paragraph 2, wherein the viral vector is selected from the group consisting of a herpesvirus and an adenovirus.

4. The composition of paragraph 2 or paragraph 3, wherein the viral vector is adeno-associated virus-9 (AAV-9).

5. The composition of any one of paragraphs 2-4, wherein the deletion comprises exon 5.

6. The composition of any one of paragraphs 2-4, wherein the deletion comprises exon 4, exon 5, exon 6 and exon 7.

7. The composition of any one of paragraphs 2-4, wherein the deletion consists of exon 5.

8. The composition of any one of paragraphs 2-4, wherein the deletion consists of exon 4, exon 5, exon 6 and exon 7.

9. An isolated mini-gamma sarcoglycan polypeptide, wherein the gamma sarcoglycan comprises at least one deletion in an exon selected from the group consisting of exon 4, exon 5, exon 6 and exon 7.

10. The mini-gamma sarcoglycan polypeptide of paragraph 9 that comprises a sequence as set forth in SEQ ID NO: 7 or SEQ ID NO: 8.

11. An isolated polypeptide that is at least about 75%, at least about 80%, at least about 85%, at least about 90%, at least about 95%, at least about 99% or 100% identical to the mini-gamma sarcoglycan polypeptide of paragraph 9 or paragraph 10.

12. A pharmaceutical composition comprising the mini-gamma sarcoglycan polypeptide of any one of paragraphs 9-11 and a pharmaceutically acceptable carrier, diluent, or excipient.

13. The composition of any one of paragraphs 2-8 or 12, further comprising an additional therapeutic agent.

14. The composition of paragraph 13, wherein the additional therapeutic agent is selected from the group consisting of a glucocorticoid steroid, an angiotensin converting enzyme inhibitor, a beta adrenergic receptor blocker, an anti-fibrotic agent and a combination thereof.

15. The composition of any one of paragraphs 2-8 or 12-14, further comprising a pharmaceutically acceptable carrier, diluent, or excipient.

16. A host cell comprising the polynucleotide of paragraph 1 or the composition of any one of paragraphs 2-8.

17. A method of expressing a mini-sarcoglycan protein in a cell, the method comprising contacting the cell with the isolated polynucleotide of paragraph 1 or the composition of any one of paragraphs 2-8 or 13 under conditions that result in expression of the mini-sarcoglycan protein in the cell.

18. The method of paragraph 17, wherein the contacting occurs in vivo.

19. The method of paragraph 17 or paragraph 18, wherein the cell is a muscle cell.

20. The method of any one of paragraphs 17-19, wherein the cell is a mammalian cell.

21. The method of paragraph 20, wherein the mammalian cell is a human cell.

22. The method of paragraph 21, wherein a human comprising the human cell has muscular dystrophy.

23. The method of paragraph 22, wherein the muscular dystrophy is Limb Girdle Muscular Dystrophy type 2C (LGMD2C).

24. The method of paragraph 17, wherein the contacting occurs in vitro.

25. The method of paragraph 24, wherein the cell is a muscle cell.

26. The method of any one of paragraphs 17 or 24-25, wherein the cell is a mammalian cell.

27. The method of paragraph 26, wherein the mammalian cell is a human cell.

28. The method of paragraph 27, wherein a human comprising the human cell has muscular dystrophy.

29. A method of ameliorating Limb Girdle Muscular Dystrophy type 2C (LGMD2C) in a patient in need thereof comprising the step of administering to the patient a therapeutically effective amount of the polynucleotide of paragraph 1 or the composition of any one of paragraphs 2-8 or 12-15, thereby ameliorating LGMD2C.

30. A method of inhibiting the progression of dystrophic pathology associated with LGMD2C in a patient in need thereof comprising the step of administering to the patient a therapeutically effective amount of the polynucleotide of paragraph 1 or the composition of any one of paragraphs 2-8 or 12-15, thereby inhibiting the progression of dystrophic pathology.

31. A method of improving muscle function in a patient suffering from Limb Girdle Muscular Dystrophy type 2C (LGMD2C) comprising the step of administering to the patient a therapeutically effective amount of the polynucleotide of paragraph 1 or the composition of any one of paragraphs 2-8 or 12-15, thereby improving muscle function.

32. The method of paragraph 31 wherein the improvement is a cardiac muscle improvement.

33. The method of paragraph 31 or paragraph 32 wherein the improvement in muscle function is an improvement in muscle strength.

34. The method of paragraph 33 wherein the improvement in muscle strength is an improvement in respiratory muscle strength.

35. The method of paragraph 29 or paragraph 30 wherein the improvement in muscle function is an improvement in motor stability.

36. The method of paragraph 35 wherein the improvement in motor stability results in an improved six-minute walk test by the patient relative to a previously measured six-minute walk test by that patient.

37. A kit comprising the polynucleotide of paragraph 1, the polypeptide of any one of paragraphs 9-11 or the composition of any one of paragraphs 2-8 or 12, optionally in a container, and a package insert, package label, instructions or other labeling.

38. The kit of paragraph 37, further comprising an additional therapeutic agent.

39. The kit of paragraph 38, wherein the additional therapeutic agent is selected from the group consisting of a glucocorticoid steroid, an angiotensin converting enzyme inhibitor, a beta adrenergic receptor blocker, an anti-fibrotic agent and a combination thereof.

DETAILED DESCRIPTION OF THE INVENTION

Figure 1:
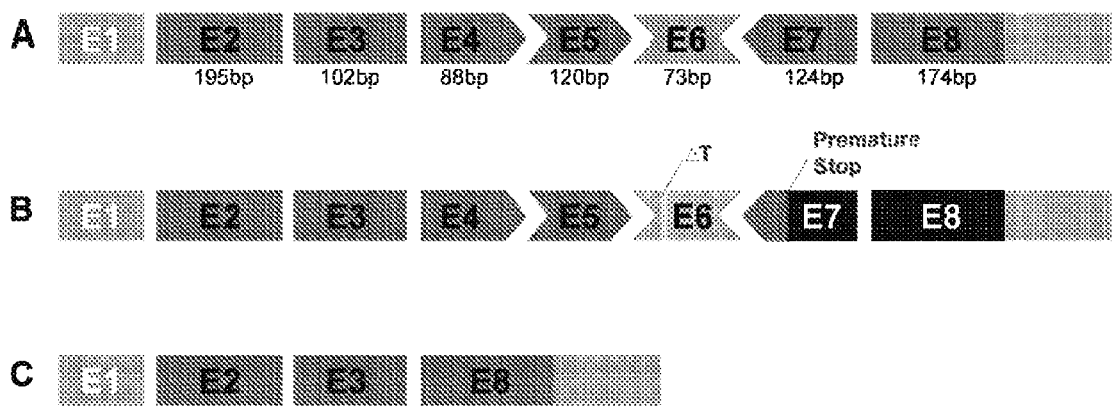
FIG. 1 shows the reading frame of the mammalian Sgcg gene before (A) and after (C) skipping exon 4-7. Deletion of one thymine in exon 6 disrupts the reading frame and is the most common LGMD2C mutation. (B). Skipping exon 4-7 restores the reading frame. Exons that follow exon "E8" and those that are labeled "E1" represent untranslated regions.

Mutations in the gene encoding γ-sarcoglycan, Sgcg, lead to muscular dystrophy, a disease with muscle degeneration, failed regeneration and muscle weakness. One strategy examined herein for the treatment of genetic forms of muscular dystrophy is exon skipping. Exclusion of certain exon(s) from final transcripts, or exon skipping, can be achieved by blocking essential splice sites using one or more antisense polynucleotides (AONs). By inducing splicing around mutation-bearing exons, an internally deleted but potentially functional protein is produced. γ-sarcoglycan is a membrane-associated protein that is part of the dystrophin protein complex, a complex that stabilizes the muscle membrane during muscle contraction. The Sgcg gene is composed of 8 exons. The most common mutation in Sgcg is the deletion of thymidine 525 in exon 6 (525ΔT), causing the production of 19 missense amino acids and a premature stop codon. Skipping exons 4-7 restores the proper protein reading frame, resulting in an internally truncated γ-sarcoglycan protein. This truncated form of γ-sarcoglycan reduces the full-length protein from 291 amino acids to 157 amino acids and retains the intracellular region, transmembrane domain and the crucial cysteine-rich motif at the carboxy-terminus.

The γ-sarcoglycan gene is conserved between human, mouse and Drosophila, and both fly and mouse models of γ-sarcoglycan gene mutations have previously been generated. The amino acid sequence of human gamma sarcoglycan is set forth in SEQ ID NO: 5, while the amino acid sequence of mouse gamma sarcoglycan is set forth in SEQ ID NO: 6. The truncated murine or human γ-sarcoglycan resulting from skipping exon 4-7 has been termed "mini-Sgcg." The amino acid sequence of human mini-Sgcg resulting from skipping exon 4-7 is set forth in SEQ ID NO: 7, while the amino acid sequence of mouse mini-Sgcg resulting from skipping exon 4-7 is set forth in SEQ ID NO: 8. The disclosure also contemplates, in various embodiments, human or mouse mini-Sgcg polypeptides in which one or more of exon 4, exon 5, exon 6 and exon 7 are deleted in any combination. Thus, mini-Sgcg polypeptides are contemplated in which exon 4-7 are variously deleted, including but not limited to combinations in which: (i) exon 4 and exon 5 are deleted; (ii) exon 5 and exon 6 are deleted; (iii) exon 4 and exon 6 are deleted; (iv) exon 4 and exon 7 are deleted; (v) exon 5 and exon 7 are deleted; (vi) exon 6 and exon 7 are deleted; (vii) exon 4, exon 5 and exon 6 are deleted; (viii) exon 5, exon 6 and exon 7 are deleted; (ix) exon 4, exon 6 and exon 7 are deleted; (x) exon 4 is deleted; (xi) exon 5 is deleted; (xii) exon 6 is deleted; or (xiii) exon 7 is deleted. The disclosure also contemplates corresponding polynucleotides that encode each of the foregoing mini-Sgcg polypeptides.

In some aspects, the disclosure provides an isolated mini-gamma sarcoglycan polypeptide, wherein the gamma sarcoglycan comprises at least one deletion in an exon selected from the group consisting of exon 4, exon 5, exon 6 and exon 7. In some embodiments, the mini-gamma sarcoglycan polypeptide of the disclosure comprises a sequence as set forth in SEQ ID NO: 7 or SEQ ID NO: 8.

In additional aspects, the disclosure provides an isolated polypeptide that is at least 75%, at least 80%, at least 85%, at least 90%, at least 95%, at least 99% or 100% identical to a mini-gamma sarcoglycan polypeptide of the disclosure. In further aspects, the disclosure provides an isolated polypeptide that is about 75%, about 80%, about 85%, about 90%, about 95% or about 99% identical to a mini-gamma sarcoglycan polypeptide of the disclosure. In still further aspects, the disclosure provides an isolated polypeptide that is at least 90% to about 100%, or at least 95% to about 100%, or at least about 95% to about 99% identical to a mini-gamma sarcoglycan polypeptide of the disclosure.

Figure 2:
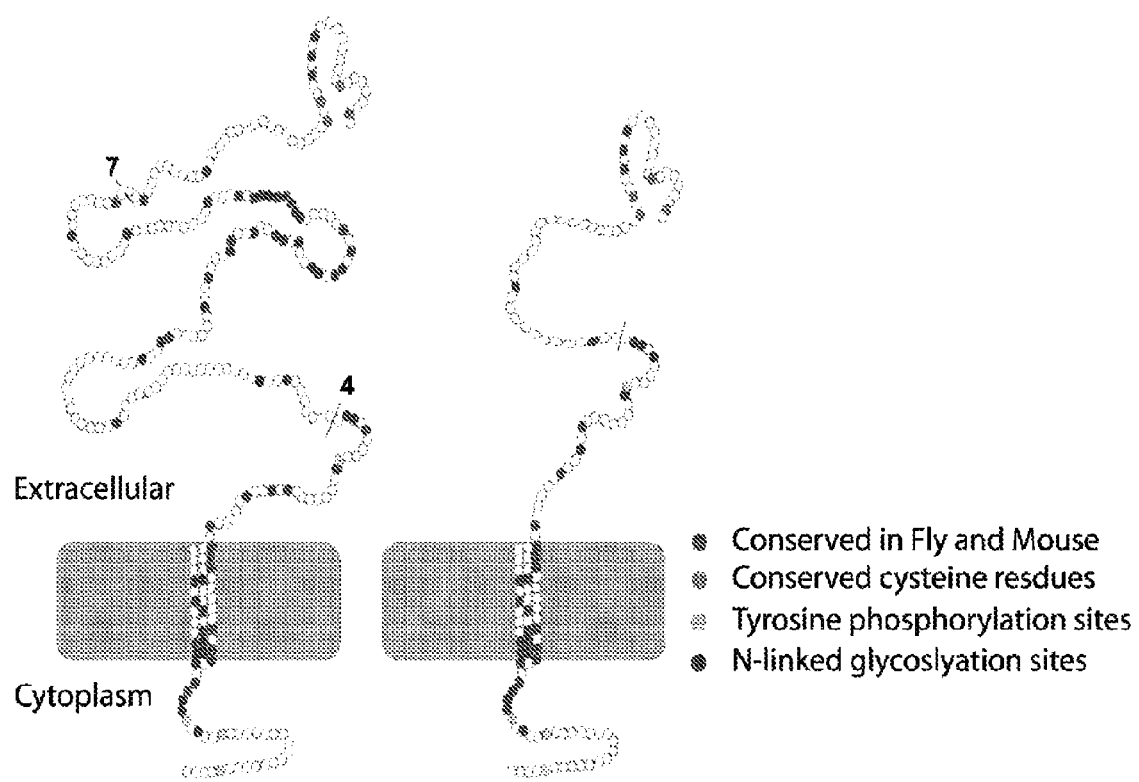
FIG. 2 depicts the structure of full-length γ-sarcoglycan (left) and the internally truncated γ-sarcoglycan after exon 4-7 is skipped (right). Conserved amino acids are shown.

Data provided herein demonstrates that the mini-Sgcg protein is produced in transgenic Drosophila, where it localizes normally to the plasma membrane. The structures of the full-length γ-sarcoglycan and the truncated protein after exon skipping are shown in FIGS. 1 and 2, respectively.

The disclosure thus provides one or more isolated antisense polynucleotide(s) wherein the one or more polynucleotide(s) specifically hybridizes to an exon target region of a gamma sarcoglycan RNA, wherein the exon is selected from the group consisting of exon 4 (SEQ ID NO: 1), exon 5 (SEQ ID NO: 2), exon 6 (SEQ ID NO: 3), exon 7 (SEQ ID NO: 4) and a combination thereof.

As used herein, "hybridization" means an interaction between two or three strands of nucleic acids by hydrogen bonds in accordance with the rules of Watson-Crick DNA complementarity, Hoogstein binding, or other sequence-specific binding known in the art. Hybridization can be performed under different stringency conditions known in the art. "Specifically hybridize," as used herein, is hybridization that allows for a stabilized duplex between polynucleotide strands that are complementary or substantially complementary. For example, a polynucleotide strand having 21 nucleotide units can base pair with another polynucleotide of 21 nucleotide units, yet only 19 bases on each strand are complementary or substantially complementary, such that the "duplex" has 19 base pairs. The remaining bases may, for example, exist as 5' and/or 3' overhangs. Further, within the duplex, 100% complementarity is not required; substantial complementarity is allowable within a duplex. Substantial complementarity refers to 75% or greater complementarity. For example, a mismatch in a duplex consisting of 19 base pairs results in 94.7% complementarity, rendering the duplex substantially complementary.

It is noted here that, as used in this specification and the appended claims, the singular forms "a," "an," and "the" include plural reference unless the context clearly dictates otherwise.

It is also noted that the term "about" as used herein is understood to mean approximately.

Antisense Polynucleotides/Polynucleotide Design

According to a first aspect of the invention, there is provided an antisense polynucleotide capable of binding to a selected target to induce exon skipping. To induce exon skipping in exons of the gamma sarcoglycan gene transcript, the antisense polynucleotide is selected based on the exon sequences shown in Tables 1 and 2. The disclosure also provides a combination or "cocktail" of two or more antisense polynucleotides capable of binding to a selected target or targets to induce exon skipping. The exon skipping contemplated herein induces exclusion of exons 4, 5, 6, and/or 7 so as to generate an in-frame, internally truncated gamma sarcoglycan protein. Excluding exons 4, 5, 6 and 7 results in the generation of an internally truncated protein lacking 135 amino acids, while deleting exon 5 results in an internally deleted, in-frame protein lacking 40 amino acids. The internally truncated proteins, termed mini-Sgcg, retains the capacity to interact with dystrophin and its associated proteins and stabilize cardiac and skeletal muscle cells.

Within the context of the disclosure, preferred target site(s) are those involved in mRNA splicing (i.e., splice donor sites, splice acceptor sites or exonic splicing enhancer elements). Splicing branch points and exon recognition sequences or splice enhancers are also potential target sites for modulation of mRNA splicing.

Thus, in various embodiments, one, two three, four, five, six, seven, eight, nine, ten, eleven, twelve, thirteen, fourteen, fifteen or more antisense polynucleotides are used to induce exon skipping of a gamma sarcoglycan nucleic acid. The choice of the number of antisense polynucleotides can be determined empirically by one of ordinary skill in the art. The person of ordinary skill can individually test the relative ability of compositions comprising one, two three, four or more antisense polynucleotides to produce a protein product of interest in vitro. Briefly, and in one specific embodiment, a composition comprising a single antisense polynucleotide that is designed to specifically hybridize (i.e., block) a splice acceptor site in exon 4 of a gamma sarcoglycan nucleic acid is added to a culture of fibroblasts obtained from a patient harboring a mutation in gamma sarcoglycan. Next, the fibroblasts are induced to adopt a myogenic lineage via forced MyoD expression (see Example 2 for details), and the resulting myotubes are tested for surface expression of a mini-Sgcg protein via, for example and without limitation, an immunofluorescence experiment. Further immunofluorescent analysis of the myotubes can be conducted to identify whether additional sarcoglycans (i.e., α-, β- and δ-sarcoglycan) are co-localized with mini-Sgcg in myotubes. Such co-localization of the members of the sarcoglycan complex associated with muscle membranes indicates that the mini-Sgcg that is produced following administration of the composition comprising a single antisense polynucleotide is able to effectively induce exon skipping of the gamma sarcoglycan nucleic acid to result in a truncated protein that retained its ability to associate with the other members of the sarcoglycan complex, as well as embed in a muscle membrane. Similar experiments may be conducted with compositions that individually comprise two, three, four, five or more antisense polynucleotides, each designed to specifically hybridize to an exon of a gamma sarcoglycan nucleic acid.

To identify and select antisense polynucleotides suitable for use in the modulation of exon skipping, a nucleic acid sequence whose function is to be modulated must first be identified. This may be, for example, a gene (or mRNA transcribed form the gene) whose expression is associated with a particular disorder or disease state, or a nucleic acid molecule from an infectious agent. Within the context of the disclosure, suitable target site(s) are those involved in mRNA splicing (e.g., splice donor sites, splice acceptor sites, or exonic splicing enhancer elements). Splicing branch points and exon recognition sequences or splice enhancers are also potential target sites for modulation of mRNA splicing contemplated by the disclosure.

TABLE 2

Table of exon coordinates based on the UCSC Human Genome Build 19.

| | exon start | exon end | exon start + 30 | exon end + 30 |
|---|---|---|---|---|
| exon 4 | 23824768 | 23824856 | 23824738 | 23824886 |
| exon 5 | 23853497 | 23853617 | 23853467 | 23853647 |
| exon 6 | 23869553 | 23869626 | 23869523 | 23869656 |
| exon 7 | 23894775 | 23894899 | 23894725* | 23894929 |

Sgcg exons per UCSC hg19, transcript NM_000231
*−50 from exon start because of T rich region Those of skill in the art can readily design antisense polynucleotides according to the present disclosure. For example, general teachings in the art include, but are not limited to, Aartsma-Rus et al., Methods Mol Biol. 867: 117-29 (2012); Aartsma-Rus et al., Methods Mol Biol. 867: 97-116 (2012); van Roon-Mom et al., Methods Mol Biol. 867: 79-96 (2012), each of which is incorporated herein by reference. General guidelines also include attempting to avoid 3 consecutive G or C nucleotides, choosing lengths and sequences that favor self structure (hairpinning will be avoided), and avoiding those sequences likely to form primer dimers. In some embodiments, an antisense polynucleotide of the disclosure is one that is designed to specifically hybridize to an exon or an intron-exon boundary, such that the antisense polynucleotide specifically hybridizes to a sequence that is completely within an exon of a gamma sarcoglycan nucleic acid, or about one nucleotide of the antisense polynucleotide spans said intron-exon boundary when the antisense polynucleotide is specifically hybridized to the gamma sarcoglycan nucleic acid. In some embodiments wherein the antisense polynucleotide specifically hybridizes to a sequence that is completely within an exon, it is contemplated that a terminus of the antisense polynucleotide is about 1, 2, 3, 4, 5, 6, 7, 8, 9, 10 or more nucleotides from a terminus of the exon. The intron-exon boundary for each of exons 4, 5, 6, and 7 is shown in Table 1. In further embodiments, an antisense polynucleotide of the disclosure is one that is designed to specifically hybridize to an intron-exon boundary of a gamma sarcoglycan nucleic acid, such that about 2, 3, 4, 5, 6, 7, 8, 9, 10 or more nucleotides of the antisense polynucleotide span said intron-exon boundary. It is understood that a nucleotide can "span the intron-exon boundary" on either the exon side or intron side. Thus, an antisense polynucleotide that specifically and predominantly hybridizes to intronic sequence and only hybridizes to one nucleotide of an adjoining exon would "span the intron-exon boundary" by one nucleotide. Similarly, an antisense polynucleotide that specifically hybridizes to exonic sequence and only hybridizes to one nucleotide of an adjoining intron would "span the intron-exon boundary" by one nucleotide. In any of the aforementioned embodiments, the antisense polynucleotide is at least about 10 nucleotides and up to about 15, 20, 25, 30, 35, 40, 45, 50 or more nucleotides in length. Lengths of antisense polynucleotides contemplated by the disclosure are discussed in more detail below.

In some aspects, the disclosure provides pharmaceutical compositions comprising an antisense polynucleotide to induce exon skipping of a gamma sarcoglycan nucleic acid, such that a "mini-Sgcg" protein is produced that has the ability to (a) effectively associate with other members of the sarcoglycan complex (i.e., α-, β- and δ-sarcoglycan) and (b) correctly embed in a muscle membrane. In some embodiments, methods described herein result in the restoration of a sarcoglycan at a muscle membrane surface, such that about 1% of the gamma sarcoglycan protein is restored relative to the amount of gamma sarcoglycan protein at a muscle membrane in the absence of administration of the pharmaceutical composition. In further embodiments, methods described herein result in the restoration of a sarcoglycan protein at the muscle membrane surface, such that about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 2-fold, about 3-fold, about 4-fold, about 5-fold, about 6-fold, about 7-fold, about 8-fold, about 9-fold, about 10-fold or more of the gamma sarcoglycan protein is restored relative to the amount of gamma sarcoglycan protein at the muscle membrane in the absence of administration of the pharmaceutical composition. Such restoration of gamma sarcoglycan protein at the muscle membrane can be determined by one of ordinary skill in the art by, for example and without limitation, obtaining a muscle biopsy from the patient and performing immunofluorescence with an antibody that has specific binding affinity for mini-Sgcg protein.

Polynucleotides

Products, uses and methods of the disclosure comprise one or more polynucleotides. As used herein, a "polynucleotide" is an oligomer comprised of nucleotides. A polynucleotide may be comprised of DNA, RNA modified forms thereof, or a combination thereof.

The term "nucleotide" or its plural as used herein is interchangeable with modified forms as discussed herein and otherwise known in the art. In certain instances, the art uses the term "nucleobase" which embraces naturally occurring nucleotides as well as modifications of nucleotides that can be polymerized. Thus, nucleotide or nucleobase means the naturally occurring nucleobases adenine (A), guanine (G), cytosine (C), thymine (T) and uracil (U) as well as non-naturally occurring nucleobases such as xanthine, diaminopurine, 8-oxo-N6-methyladenine, 7-deazaxanthine, 7-deazaguanine, N4,N4-ethanocytosin, N',N'-ethano-2,6-diaminopurine, 5-methylcytosine (mC), 5-($C_3$-$C_6$)-alkynylcytosine, 5-fluorouracil, 5-bromouracil, pseudoisocytosine, 2-hydroxy-5-methyl-4-tr-iazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which is hereby incorporated by reference in its entirety). In various aspects, polynucleotides also include one or more "nucleosidic bases" or "base units" which include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles (e.g., 5-nitroindole), and optionally substituted hypoxanthine. Other desirable universal bases include pyrrole, and diazole or triazole derivatives, including those universal bases known in the art.

Polynucleotides may also include modified nucleobases. A "modified base" is understood in the art to be one that can pair with a natural base (e.g., adenine, guanine, cytosine, uracil, and/or thymine) and/or can pair with a non-naturally occurring base. Exemplary modified bases are described in EP 1 072 679 and WO 97/12896, the disclosures of which are incorporated herein by reference. Modified nucleobases include, without limitation, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2 (3H)-one), G-clamps such as a substituted phenoxazine cytidine (e.g. 9-(2-aminoethoxy)-H-pyrimido[5,4-b][1,4] benzoxazin-2(3H)-one), carbazole cytidine (2H-pyrimido[4, 5-b]indol-2-one), pyridoindole cytidine (H-pyrido[3',2':4,5] pyrrolo[2,3-d]pyrimidin-2-one). Modified bases may also include those in which the purine or pyrimidine base is replaced with other heterocycles, for example 7-deazaadenine, 7-deazaguanosine, 2-aminopyridine and 2-pyridone. Additional nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, Angewandte Chemie, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity of the polynucleotide and include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects, combined with 2'-O-methoxyethyl sugar modifications. See, U.S. Pat. No. 3,687,808, U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,750,692 and 5,681,941, the disclosures of which are incorporated herein by reference.

Modified polynucleotides are contemplated for use wherein both one or more sugar and/or one or more inter-nucleotide linkage of the nucleotide units in the polynucleotide is replaced with "non-naturally occurring" sugars (i.e., sugars other than ribose or deoxyribose) or internucleotide linkages, respectively. In one aspect, this embodiment contemplates a peptide nucleic acid (PNA). In PNA compounds, the sugar-backbone of a polynucleotide is replaced with an amide-containing (e.g., peptide bonds between N-(2-aminoethyl)-glycine units) backbone. See, for example U.S. Pat. Nos. 5,539,082; 5,714,331; and 5,719,262, and Nielsen et al., Science, 1991, 254, 1497-1500, the disclosures of which are herein incorporated by reference.

Modified polynucleotides may also contain one or more substituted sugar groups. In one aspect, a modification of the sugar includes Locked Nucleic Acids (LNAs) in which the 2'-hydroxyl group is linked to the 3' or 4' carbon atom of the sugar ring, thereby forming a bicyclic sugar group. The linkage is in certain aspects a methylene ($-CH_2-$)$_n$ group bridging the 2' oxygen atom and the 4' carbon atom wherein n is 1 or 2. LNAs and preparation thereof are described in WO 98/39352 and WO 99/14226, the disclosures of which are incorporated herein by reference.

To avoid degradation of pre-mRNA during duplex formation with the antisense polynucleotides, the antisense polynucleotides used in the method may be adapted to minimize or prevent cleavage by endogenous RNase H. This property is advantageous because the treatment of the RNA with the unmethylated polynucleotides either intracellularly or in crude extracts that contain RNase H leads to degradation of the pre-mRNA:antisense polynucleotide duplexes. Any form of modified antisense polynucleotide that is resistant to such degradation, or does not induce such degradation, is contemplated by the disclosure. Non-limiting examples of antisense molecules which, when duplexed with RNA, are not cleaved by cellular RNase H are polynucleotides comprising 2'-O-methyl derivatives of nucleotides. 2'-O-methyl-oligoribonucleotides are very stable in a cellular environment and in animal tissues, and their duplexes with RNA have higher $T_m$ values than their ribo- or deoxyribo-counterparts.

Antisense polynucleotides that do not activate RNase H can be made in accordance with known techniques (see, for example and without limitation, U.S. Pat. No. 5,149,797). Such antisense polynucleotides, which may be deoxyribonucleotide or ribonucleotide sequences, simply contain any structural modification which sterically hinders or prevents binding of RNase H to a duplex molecule containing the polynucleotide as one member thereof, which structural modification does not substantially hinder or disrupt duplex formation. Because the portions of the polynucleotide involved in duplex formation are substantially different from those portions involved in RNase H binding thereto, numerous antisense molecules that do not activate RNase H are available. (Activation is used in this sense to refer to RNase H degradation, whether as a result of a substrate not being susceptible to such degradation or such substrate failing to induce degradation.) For example, such antisense molecules may be polynucleotides wherein at least one, or all, of the inter-nucleotide bridging phosphate residues are modified phosphates, such as methyl phosphonates, methyl phosphorothioates, phosphoromorpholidates, phosphoropiperazidates and/or phosphoramidates. For example, every other one of the internucleotide bridging phosphate residues may be modified as described. In another non-limiting example, such antisense polynucleotides are polynucleotides wherein at least one, or all, of the nucleotides contain a 2' carbon bound to a lower alkyl moiety (e.g., $C_1$-$C_4$, linear or branched, saturated or unsaturated alkyl, such as methyl, ethyl, ethenyl, propyl, 1-propenyl, 2-propenyl, and isopropyl). For example, every other one of the nucleotides may be modified as described.

Methods of making polynucleotides of a predetermined sequence are well-known. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both polyribonucleotides and polydeoxyribonucleotides (the well-known methods of synthesizing DNA are also useful for synthesizing RNA). Polyribonucleotides can also be prepared enzymatically. Non-naturally occurring nucleobases can be incorporated into the polynucleotide, as well. See, e.g., U.S. Pat. No. 7,223,833; Katz, J. Am. Chem. Soc., 74:2238 (1951); Yamane, et al., J. Am. Chem. Soc., 83:2599 (1961); Kosturko, et al., Biochemistry, 13:3949 (1974); Thomas, J. Am. Chem. Soc., 76:6032 (1954); Zhang, et al., J. Am. Chem. Soc., 127:74-75 (2005); and Zimmermann, et al., J. Am. Chem. Soc., 124:13684-13685 (2002).

Polynucleotides contemplated herein range from about 5 nucleotides to about 50 nucleotides in length. In some embodiments, the polynucleotide is between at least 5 nucleotides and at least 20 nucleotides, between at least 5 nucleotides and at least 30 nucleotides or between at least 5 nucleotides and at least 50 nucleotides.

In further embodiments, a polynucleotide contemplated by the disclosure is about 5 to about 60, 70, 80, 90, 100 or more nucleotides in length, about 5 to about 90 nucleotides in length, about 5 to about 80 nucleotides in length, about 5 to about 70 nucleotides in length, about 5 to about 60 nucleotides in length, about 5 to about 50 nucleotides in length about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, and all polynucleotides intermediate in length of the sizes specifically disclosed to the extent that the polynucleotide is able to achieve the desired result. Accordingly, polynucleotides of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleotides in length are contemplated.

The polynucleotides of the disclosure are approximately 40% GC to about 60% GC, with a Tm of about 48° C. or higher.

Another modification of the polynucleotides of the invention involves chemically linking the polynucleotide to one or more moieties or conjugates that enhance the activity, cellular distribution or cellular uptake of the polynucleotide. Such moieties include, but are not limited to, lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety.

Therapeutic Agents

The compounds of the disclosure also can be used as a prophylactic or therapeutic, which may be utilized for the purpose of treatment of a genetic disease.

In one embodiment the disclosure provides antisense polynucleotides that bind to a selected target in the gamma sarcoglycan pre-mRNA to induce efficient and consistent exon skipping described herein in a therapeutically or prophylactically effective amount admixed with a pharmaceutically acceptable carrier, diluent, or excipient.

A pharmaceutically acceptable carrier refers, generally, to materials that are suitable for administration to a subject wherein the carrier is not biologically harmful, or otherwise, causes undesirable effects. Such carriers are typically inert ingredients of a medicament. Typically a carrier is administered to a subject along with an active ingredient without causing any undesirable biological effects or interacting in a deleterious manner with any of the other components of a pharmaceutical composition in which it is contained. Suitable pharmaceutical carriers are described in Martin, Remington's Pharmaceutical Sciences, 18th Ed., Mack Publishing Co., Easton, Pa., (1990), incorporated by reference herein in its entirety.

In a more specific form of the disclosure there are provided pharmaceutical compositions comprising therapeutically effective amounts of an antisense polynucleotide together with pharmaceutically acceptable diluents, preservatives, solubilizers, emulsifiers, adjuvants and/or carriers. Such compositions include diluents of various buffer content (e.g., phosphate, Tris-HCl, acetate), pH and ionic strength and additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol). The material may be incorporated into particulate preparations of polymeric compounds such as, for example and without limitation, polylactic acid or polyglycolic acid, or into liposomes. Hylauronic acid may also be used. Such compositions may influence the physical state, stability, rate of in vivo release, and rate of in vivo clearance of the disclosed compositions. The compositions may be prepared in liquid form, or may be in dried powder, such as lyophilized form.

It will be appreciated that pharmaceutical compositions provided according to the disclosure may be administered by any means known in the art. Preferably, the pharmaceutical compositions for administration are administered by injection, orally, or by the pulmonary, or nasal route. The antisense polynucleotides are, in various embodiments, delivered by intravenous, intra-arterial, intraperitoneal, intramuscular, or subcutaneous routes of administration.

The antisense molecules of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such pro-drugs, and other bioequivalents.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

For polynucleotides, preferred examples of pharmaceutically acceptable salts include, but are not limited to, (a) salts formed with cations such as sodium, potassium, ammonium, magnesium, calcium, polyamines such as spermine and spermidine; (b) acid addition salts formed with inorganic acids, for example hydrochloric acid, hydrobromic acid, sulfuric acid, phosphoric acid, nitric acid; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid; and (d) salts formed from elemental anions such as chlorine, bromine, and iodine. The pharmaceutical compositions of the disclosure may be administered in a number of ways depending upon whether local or systemic treatment is desired and upon the area to be treated. Administration may be topical (including ophthalmic and to mucous membranes including rectal delivery), pulmonary, e.g., by inhalation of powders or aerosols, (including by nebulizer, intratracheal, intranasal, epidermal and transdermal), oral or parenteral. Parenteral administration includes intravenous, intra-arterial, subcutaneous, intraperitoneal or intramuscular injection or infusion; or intracranial, e.g., intrathecal or intraventricular, administration. Polynucleotides with at least one 2'-O-methoxyethyl modification are believed to be particularly useful for oral administration.

The pharmaceutical formulations of the disclosure, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly bringing into association the active ingredients with liquid carriers or finely divided solid carriers or both, and then, if necessary, shaping the product.

Combination therapy with an additional therapeutic agent is also contemplated by the disclosure. Examples of therapeutic agents that may be delivered concomitantly with a composition of the disclosure include, without limitation, a glucocorticoid steroid (for example and without limitation, prednisone and deflazacort), an angiotensin converting enzyme inhibitor, a beta adrenergic receptor blocker, an anti-fibrotic agent and a combination thereof.

Gene Therapy

In some aspects, the disclosure provides methods of expressing a mini-gamma sarcoglycan in a cell. In any of the aspects or embodiments of the disclosure, the cell is a mammalian cell. In any of the aspects or embodiments of the disclosure, the cell is in a human and the human is in need of the mini-gamma sarcoglycan. Accordingly, in some aspects the disclosure provides gene therapy methods for expressing a mini-gamma sarcoglycan in a cell.

In some embodiments, a vector (e.g., an expression vector) comprising a polynucleotide of the invention to direct expression of the polynucleotide in a suitable host cell. Such vectors are useful, e.g., for amplifying the polynucleotides in host cells to create useful quantities thereof, and for expressing proteins using recombinant techniques. In some embodiments, the vector is an expression vector wherein a polynucleotide of the invention is operatively linked to a polynucleotide comprising an expression control sequence. Autonomously replicating recombinant expression constructs such as plasmid and viral DNA vectors incorporating polynucleotides of the disclosure are specifically contemplated. Expression control DNA sequences include promoters, enhancers, and operators, and are generally selected based on the expression systems in which the expression construct is to be utilized. In some embodiments, promoter and enhancer sequences are selected for the ability to increase gene expression, while operator sequences may be selected for the ability to regulate gene expression. Expression constructs of the invention may also include sequences encoding one or more selectable markers that permit identification of host cells bearing the construct. Expression constructs may also include sequences that facilitate, and preferably promote, homologous recombination in a host cell. Expression constructs of the disclosure also include, in various embodiments, sequences necessary for replication in a host cell.

Exemplary expression control sequences include promoter/enhancer sequences, e.g., cytomegalovirus promoter/enhancer [Lehner et al., J. Clin. Microbiol., 29: 2494-2502, 1991; Boshart et al., Cell, 41: 521-530, (1985)]; Rous sarcoma virus promoter [Davis et al., Hum. Gene Ther., 4: 151, (1993)]; and simian virus 40 promoter, for expression in a target mammalian cell, the promoter being operatively linked upstream (i.e., 5') of the polypeptide coding sequence (the disclosures of the cited references are incorporated herein by reference in their entirety and particularly with respect to the discussion of expression control sequences). In another variation, the promoter is a muscle-specific promoter. The polynucleotides of the invention may also optionally include a suitable polyadenylation sequence (e.g., the SV40 or human growth hormone gene polyadenylation sequence) operably linked downstream (i.e., 3') of the polypeptide coding sequence.

If desired, a polynucleotide of the disclosure also optionally comprises a nucleotide sequence encoding a secretory signal peptide fused in frame with the polypeptide sequence. The secretory signal peptide directs secretion of the polypeptide of the invention by the cells that express the polynucleotide, and is cleaved by the cell from the secreted polypeptide. The polynucleotide may further optionally comprise sequences whose only intended function is to facilitate large scale production of the vector, e.g., in bacteria, such as a bacterial origin of replication and a sequence encoding a selectable marker. However, if the vector is administered to an animal, such extraneous sequences are preferably at least partially cleaved. One can manufacture and administer polynucleotides for gene therapy using procedures that have been described in the literature for other transgenes. See, e.g., Isner et al., Circulation, 91: 2687-2692, 1995; Isner et al., Human Gene Therapy, 7: 989-1011, 1996; Wang et al., Mol Ther. 20(8):1501-7 (2012); and Zhang et al., Hum Mol Genet. 22(18): 3720-9 (2013); each of which is incorporated herein by reference in its entirety.

In some embodiments, a "naked" transgene encoding a mini-gamma sarcoglycan described herein (i.e., a transgene without a viral, liposomal, or other vector to facilitate transfection) is employed.

Vectors also are useful for "gene therapy" treatment regimens, wherein, for example, a polynucleotide encoding a mini-gamma sarcoglycan is introduced into a subject suffering from or at risk of suffering from a muscular dystrophy in a form that causes cells in the subject to express the mini-gamma sarcoglycan in vivo. Any suitable vector may be used to introduce a polynucleotide that encodes a mini-gamma sarcoglycan into the host. Exemplary vectors that have been described in the literature include replication deficient retroviral vectors, including but not limited to lentivirus vectors [Kim et al., J. Virol., 72(1): 811-816, (1998); Kingsman & Johnson, Scrip Magazine, October, 1998, pp. 43-46]; parvoviral vectors, such as adeno-associated viral (AAV) vectors [U.S. Pat. Nos. 5,474,9351; 5,139,941; 5,622,856; 5,658,776; 5,773,289; 5,789,390; 5,834,441; 5,863,541; 5,851,521; 5,252,479; Gnatenko et al., J. Invest. Med., 45: 87-98, (1997)]; adenoviral (AV) vectors [U.S. Pat. Nos. 5,792,453; 5,824,544; 5,707,618; 5,693,509; 5,670,488; 5,585,362; Quantin et al., Proc. Natl. Acad. Sci. USA, 89: 2581-2584, (1992); Stratford Perricaudet et al., J. Clin. Invest., 90: 626-630, (1992); and Rosenfeld et al., Cell, 68: 143-155, (1992)]; an adenoviral adeno-associated viral chimeric [U.S. Pat. No. 5,856,152] or a vaccinia viral or a herpesviral vector [U.S. Pat. Nos. 5,879,934; 5,849,571; 5,830,727; 5,661,033; 5,328,688]; Lipofectin mediated gene transfer (BRL); liposomal vectors [U.S. Pat. No. 5,631,237]; and combinations thereof. Additionally contemplated by the disclosure for introducing a polynucleotide encoding a mini-gamma sarcoglycan into a subject is a plasmid vector [see, e.g., Dean, Am J Physiol Cell Physiol. 289(2): C233-45 (2005); Kaufman et al., Gene Ther. 17(9): 1098-104 (2010); Magnusson et al., J Gene Med. 13(7-8): 382-91 (2011)]. For example and without limitation, any pBR- or pUC-derived plasmid vector is contemplated. All of the foregoing documents are incorporated herein by reference in their entirety and particularly with respect to their discussion of expression vectors. Any of these expression vectors can be prepared using standard recombinant DNA techniques described in, e.g., Sambrook et al., Molecular Cloning, a Laboratory Manual, 2d edition, Cold Spring Harbor Press, Cold Spring Harbor, N.Y. (1989), and Ausubel et al., Current Protocols in Molecular Biology, Greene Publishing Associates and John Wiley & Sons, New York, N.Y. (1994). Optionally, the viral vector is rendered replication-deficient by, e.g., deleting or disrupting select genes required for viral replication.

Other non-viral delivery mechanisms contemplated include calcium phosphate precipitation [Graham and Van Der Eb, Virology, 52: 456-467, 1973; Chen and Okayama, Mol. Cell Biol., 7: 2745-2752, (1987); Rippe et al., Mol. Cell Biol., 10: 689-695, (1990)], DEAE-dextran [Gopal, Mol. Cell Biol., 5: 1188-1190, (1985)], electroporation [Tur-Kaspa et al., Mol. Cell Biol., 6: 716-718, (1986); Potter et al., Proc. Nat. Acad. Sci. USA, 81: 7161-7165, (1984)], direct microinjection [Harland and Weintraub, J. Cell Biol., 101: 1094-1099, (1985)], DNA-loaded liposomes [Nicolau and Sene, Biochim. Biophys. Acta, 721: 185-190, (1982); Fraley et al., Proc. Natl. Acad. Sci. USA, 76: 3348-3352, (1979); Felgner, Sci Am., 276(6): 102-6, (1997); Felgner, Hum Gene Ther., 7(15): 1791-3, (1996)], cell sonication [Fechheimer et al., Proc. Natl. Acad. Sci. USA, 84: 8463-8467, (1987)], gene bombardment using high velocity microprojectiles [Yang et al., Proc. Natl. Acad. Sci USA, 87: 9568-9572, (1990)], and receptor-mediated transfection [Wu and Wu, J. Biol. Chem., 262: 4429-4432, (1987); Wu and Wu, Biochemistry, 27: 887-892, (1988); Wu and Wu, Adv. Drug Delivery Rev., 12: 159-167, (1993)].

The expression vector (or the mini-gamma sarcoglycan discussed herein) may be entrapped in a liposome.

In some embodiments, transferring a naked DNA expression construct into cells is accomplished using particle bombardment, which depends on the ability to accelerate DNA coated microprojectiles to a high velocity allowing them to pierce cell membranes and enter cells without killing them [Klein et al., Nature, 327: 70-73, (1987)]. Several devices for accelerating small particles have been developed. One such device relies on a high voltage discharge to generate an electrical current, which in turn provides the motive force [Yang et al., Proc. Natl. Acad. Sci USA, 87: 9568-9572, (1990)]. The microprojectiles used have consisted of biologically inert substances such as tungsten or gold beads.

In embodiments employing a viral vector, preferred polynucleotides still include a suitable promoter and polyadenylation sequence as described above. Moreover, it will be readily apparent that, in these embodiments, the polynucleotide further includes vector polynucleotide sequences (e.g., adenoviral polynucleotide sequences) operably connected to the sequence encoding a polypeptide of the disclosure.

The disclosure further provides a cell that comprises the polynucleotide or the vector, e.g., the cell is transformed or transfected with a polynucleotide encoding a mini-gamma sarcoglycan of the disclosure or the cell is transformed or transfected with a vector comprising a polynucleotide encoding the mini-gamma sarcoglycan.

Polynucleotides of the disclosure may be introduced into the host cell as part of a circular plasmid, or as linear DNA comprising an isolated protein coding region or a viral vector. Methods for introducing DNA into the host cell, which are well known and routinely practiced in the art, include transformation, transfection, electroporation, nuclear injection, or fusion with carriers such as liposomes, micelles, ghost cells, and protoplasts. As stated above, such host cells are useful for amplifying the polynucleotides and also for expressing the polypeptides of the invention encoded by the polynucleotide. The host cell may be isolated and/or purified. The host cell also may be a cell transformed in vivo to cause transient or permanent expression of the polypeptide in vivo. The host cell may also be an isolated cell transformed ex vivo and introduced post-transformation, e.g., to produce the polypeptide in vivo for therapeutic purposes.

Kits

The disclosure also provides kits for treatment of a patient with a genetic disease such as LGMD2C. In one aspect, the kit comprises an antisense polynucleotide as disclosed herein, optionally in a container, and a package insert, package label, instructions or other labeling.

In a further embodiment, a kit is provided that comprises an additional polynucleotide, wherein the additional polynucleotide specifically hybridizes to an exon in a gamma sarcoglycan RNA.

Those of ordinary skill in the art will appreciate that applications of the above method has wide application for identifying antisense molecules suitable for use in the treatment of many other diseases.

EXAMPLES

Example 1

Rescue Efficiency of Mammalian Full Length γ-Sarcoglycan and Mini-Sgcg in Sarcoglycan Null Flies The sarcoglycans are conserved between *Drosophila* and mammals. γ-sarcoglycan null flies develop symptoms similar to mammals. Transgenic flies expressing full-length murine γ-sarcoglycan and mini-Sgcg, were generated and it was found that mini-Sgcg protein correctly localizes at the plasma membrane of fly muscle cells.

γ/δ-sarcoglycan null flies ($Sgcd^{840}$) were previously generated and characterized [Allikian et al., Hum Mol Genet 16: 2933-2943 (2007)]. Using PCR and Southern blot, it has been shown that exons 1 to 3 and partial exon 4 out of the 6 exons in the *Drosophila* Sgcd gene is deleted in $Sgcd^{840}$ flies.

To determine whether mini-Sgcg retains the function of the full-length protein, the UAS-GAL4 system was utilized [Brand et al., Development. 118: 401-15 (1993)] to express two different sarcoglycan constructs. GAL4 is a transcription factor that recognizes a specific enhancer sequence called UAS.

Figure 3:
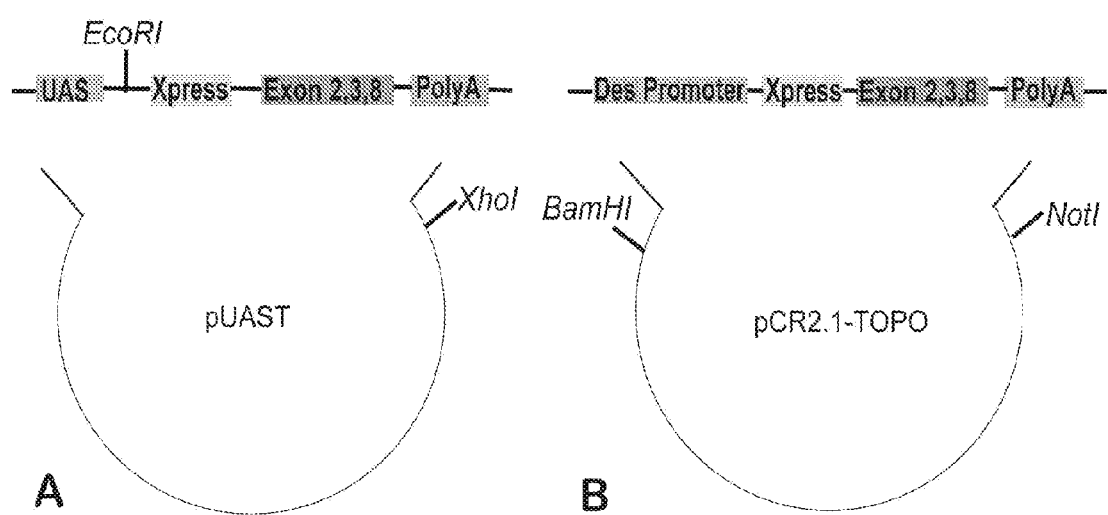
FIG. 3 depicts vector maps of mini-Sgcg constructs in transgenic flies (A) and transgenic mice (B). UAS is the enhancer sequence specifically recognized by Gal4. The desmin (Des) promoter is muscle specific. Preliminary data has shown mini-Sgcg is produced in UAS-mini-Sgcg transgenic flies and in Des-mini-Sgcg transfected muscle cells in culture. Note that mini-Sgcg produced from both transgenes is tagged with the Xpress epitope tag.

The first construct expresses the full coding sequence of murine Sgcg gene from exon 2 to exon 8, referred to as UAS-Sgcg. The second construct comprises the sequence of an Xpress epitope tag and exon 2, exon 3 and exon 8 of murine Sgcg gene only, referred to as UAS-mini-Sgcg (FIG. 1). The shorter construct retains the coding sequence of an intact intracellular domain, transmembrane domain and part of the extracellular domain including the essential carboxyl-terminus (FIG. 2). A comparison of the constructs used in *Drosophila* and mouse is depicted in FIG. 3. One UAS-Sgcg and one UAS-mini-Sgcg transgenic line were generated in matched genetic backgrounds. A Mef2-GAL4 stock was also obtained. Mef2 is a muscle specific driver that promotes GAL4 expression in both heart and skeletal muscle tissue. Flies carrying both Mef2-GAL4 and UAS-Sgcg or UAS-mini-Sgcg produce Sgcg or mini-Sgcg protein specifically in the heart tube and in muscle tissue. To express the full-length and mini-Sgcg in mutant flies, $Sgcd^{840}$, Mef2-GAL4 virgin females were crossed to either UAS-Sgcg/+ or UAS-mini-Sgcg/+ male flies. Since the Sgcd gene is located on X chromosome, all the male progeny from each cross were null for Sgcd, with half carrying both GAL4 and UAS transgenes. The other half served as an internal negative control. This comparison minimizes the effects of environment and genetic background on behavior assays. Wild-type flies with matched age and genetic background served as the positive control.

Figure 4:
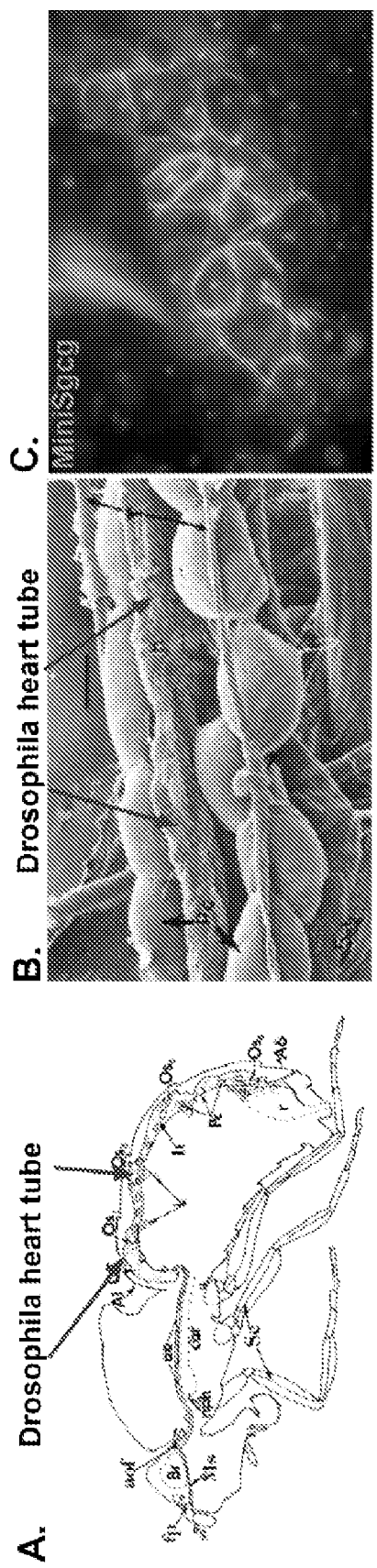
FIG. 4 shows that the *Drosophila* heart tube is a thin-walled structure that runs along the dorsum of the adult fly (A). B shows an EM image of the heart tube (h and arrows). A and B are from Curtis, Morphology 240: 225 (1999). C shows the membrane localized staining from the mini-Sgcg transgene expressing mini-Sgcg in Sgcg$^{840}$ flies in the heart tube using a Tinman GAL4.
Figure 5:
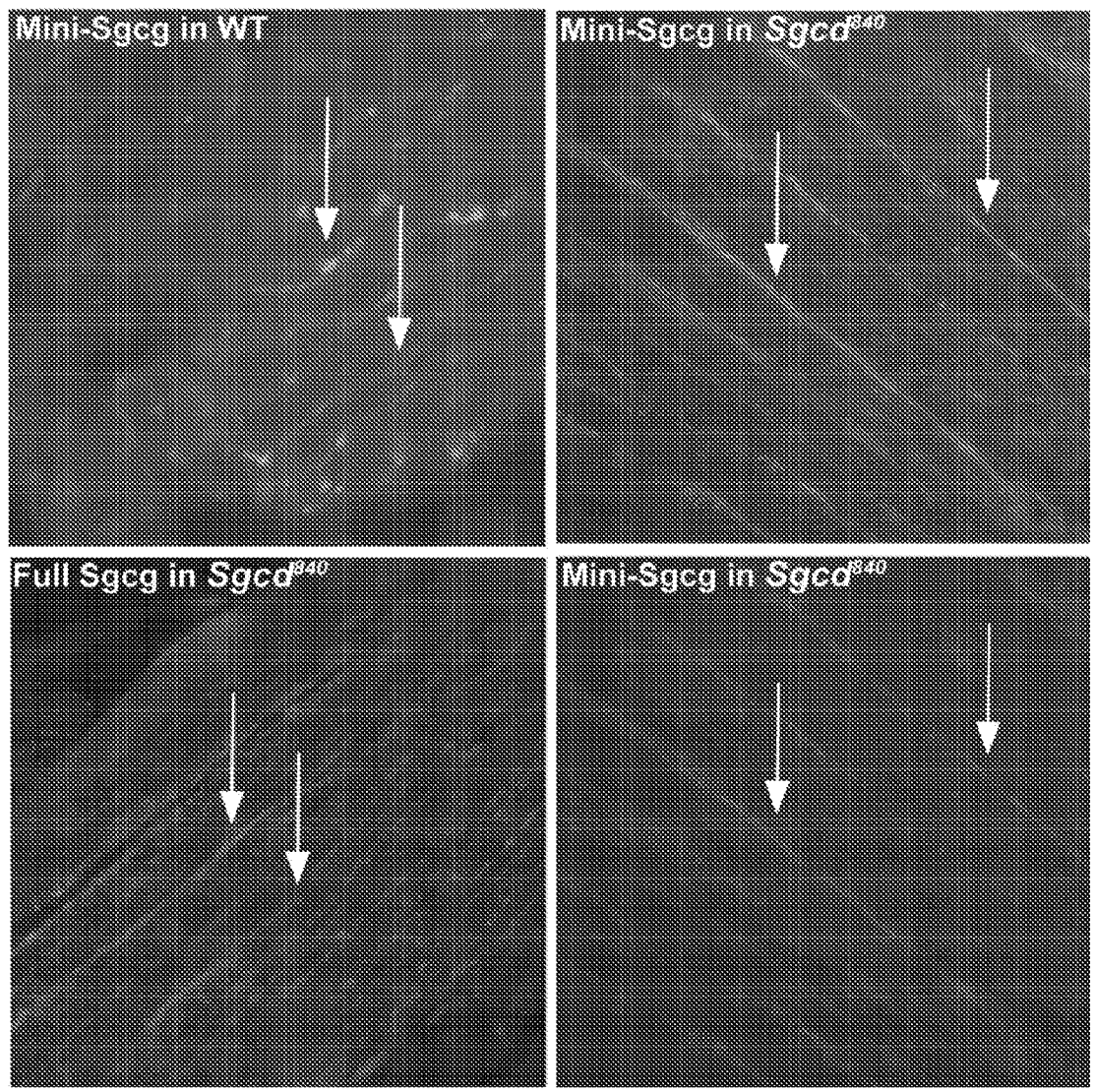
FIG. 5 depicts that full-length Sgcg and mini-Sgcg are expressed and localize correctly to the plasma membrane of transgenic fly skeletal muscle cells. Muscle cells are aligned parallel to each other.

The data showed that mini-Sgcg has distinct plasma membrane localization in $Sgcd^{840}$ fly heart tubes (FIG. 4) and in body muscle (FIG. 5). This pattern is similar to full length Sgcg (FIG. 5). Studies in human muscle, mice, and cell expression systems suggest that sarcoglycan complex assembly is required for the shuttling of γ-sarcoglycan to the plasma membrane [Allikian et al., Traffic 8: 177-83 (2007); Chen et al., Exp Cell Res. 312: 1610-25 (2006); Crosbie et al., Hum Mol Genet. 9:2019-27 (2000)]. Thus the correct subcellular localization of both proteins implies interaction with the fly sarcoglycan subunits, highlighting the conservation between murine and fly γ-sarcoglycan. More importantly, the results indicated that mini-Sgcg protein retains the function of interacting with other components of the dystrophin complex.

Skeletal Muscle Structure and Function in Transgenically Rescued Flies

Patients with LGMD2C display distinct muscle histology from healthy individuals, including loss of mature muscle fibers, abnormal deposition of fibrotic or fatty tissue and immune cells infiltration [Dubowitz, Muscle disorders in childhood. Saunders, Philadelphia. xiii, 282 (1978)]. $Sgcd^{840}$ flies show increased detachment of flight muscle from exoskeleton, and this finding is more prominent if flies are allowed to exercise [Goldstein et al., Hum Mol Genet. 20: 894-904 (2011)]. To encourage muscle usage, flies are kept in a 20×20×20 cm box instead of standard vials so that they can fly at ease. Flies are aged to 28 days before harvesting for histological examination. Specifically, thoraces are collected, sectioned and stain with hematoxylin and eosin (H&E) using the Carnoy fixation protocol. The frequency of flight muscle fracture between mutant flies, rescued flies and wild-type flies are then compared.

Similar to human patients, $Sgcd^{840}$ flies develop impaired locomotive ability over time [Allikian et al., Hum Mol Genet 16: 2933-43 (2007)]. Motility defects are measured using a negative geotaxis assay. Different from most apparatus for bulk measurement, a more "individualized" apparatus was designed that can provide the walking ability measurement of an individual fly as precise as 0.5 cm [Goldstein et al., Hum Mol Genet. 20: 894-904 (2011)]. The apparatus is composed of 16 vertical plastic tubes that are 13 cm long with rulers on each side. Briefly, an individual fly is placed in each tube after anesthesia, allowed to recover for 30 minutes and then tested. To test walking, the flies are then tapped to the bottom and allowed to climb up for 5 seconds. The distance that each fly travels at the end of the 5 seconds is scored. Six trials with a 1-minute interval are performed. Analysis of variance (ANOVA) with a post Tukey test is employed for data analysis in PRISM software.

Assess Heart Function Rescue Using Optical Coherence Tomography (OCT)

Figure 6:
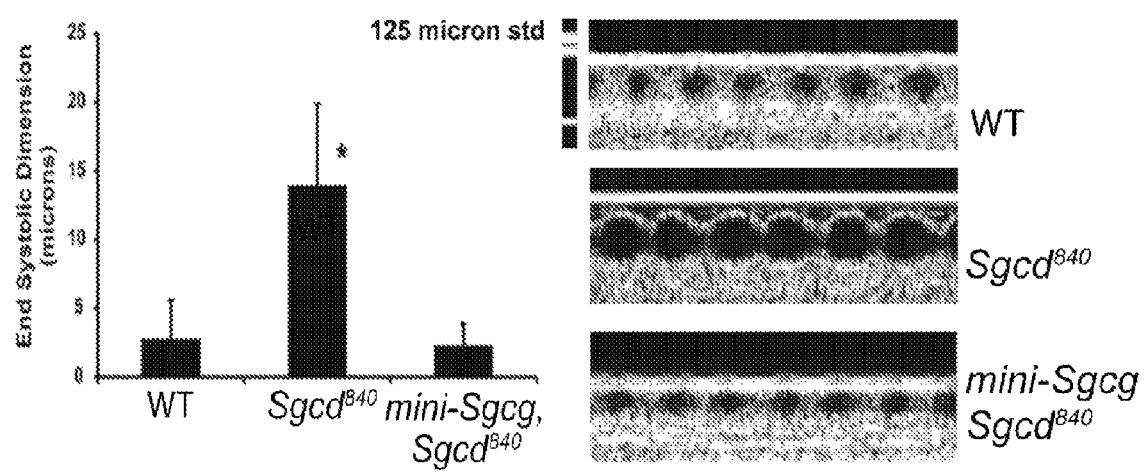
FIG. 6 depicts improved heart function in mini-Sgcg rescued Sgcd$^{840}$ flies. Shown on the left is the End Systolic Dimension (ESD). Sgcd$^{840}$ flies have increased ESD, indicating heart tube dilation. This enlargement is rescued when mini-Sgcg protein is introduced into Sgcd$^{840}$ flies via transgenesis.

Muscular dystrophy patients develop dilated cardiomyopathy due to the impaired contractility of heart muscle cells. $Sgcd^{840}$ flies also show cardiac malfunction as they age, indicated by enlarged heart tube and reduced fraction shortening [Allikian et al., Hum Mol Genet 16: 2933-43 (2007); Goldstein et al., Hum Mol Genet. 20: 894-904 (2011)]. The heart function of flies is examined by OCT [Wolf et al., Proc Natl Acad Sci USA. 103: 1394-9 (2006)]. OCT serves as the fly counterpart to the echocardiography (ECHO) used with mammals. The major difference between OCT and ECHO is that OCT measures backscattered light instead of sound. OCT determines the end systolic diameter (ESD), end diastolic diameter (EDD), fractional shortening (FS) and heart rate. Twenty to forty flies from each genotype were tested at 7-10 days of age. Data showed that mini-Sgcg expression reduced the abnormal heart tube dilation in $Sgcd^{840}$ flies (FIG. 6), indicating that the mini-Sgcg was functional. Flies will be assessed at older ages, when the cardiomyopathy is more prevalent. Importantly, the results will be compared to transgenic flies expressing full-length murine γ-sarcoglycan to determine if the degree of correction is similar between the mini-Sgcg and the full-length Sgcg.

It is expected that expression of either mini-Sgcg or full-length Sgcg will lead to rescue of disease progression in mutant flies. Specifically, it is expected that less muscle disruption, improved walking ability and restored heart function will be seen in mutant flies with the mini-Sgcg or Sgcg. It is possible that the preparation procedures of the muscle tissue might interfere with identification of muscle tears. Muscle damage induces TGFβ signaling surrounding the injury sites, which can be visualized by dad-lacZ reporter activity [Goldstein et al., Hum Mol Genet. 20: 894-904 (2011)]. The dad-lacZ reporter construct is expected to provide better visualization of muscle tearing [Goldstein et al., Hum Mol Genet. 20: 894-904 (2011)]. If the walking assay is not sensitive enough to detect the improvement brought by expression of mini-Sgcg, an alternative motility assay that enables the examination of a larger number of flies at one time will be performed [Shcherbata et al., EMBO J 26: 481-93 (2007)]. Mutant flies have reduced life span [Allikian et al., Hum Mol Genet 16: 2933-43 (2007)]. Thus, the lifespan of mini-Sgcg-rescued flies is determined, providing additional evidence of the benefits of mini-Sgcg expression, and the increased lifespan will be quantitated. Data has shown that expression of mini-Sgcg significantly improved heart function in $Sgcd^{840}$ flies, leading to the expectation that mini-Sgcg or full-length Sgcg will yield beneficial effects in preventing or treating dystrophic disease such as LGMD (e.g., LGMD2C). As a comparison, flies that express *Drosophila* Sgcd have also been generated for comparison purposes.

Example 2

Mini-Sgcg can Replace Full-Length Sgcg in the γ-Sarcoglycan Mutant Mouse Model

By characterizing the correction of mutant phenotype in an established mouse model, a more accurate prediction of the effect of replacing the full-length γ-sarcoglycan with the truncated γ-sarcoglycan in human patients can be determined.

Transgenic Mouse Expressing Mini-Sgcg in Muscle Using the Human Desmin Promoter with the Mini-Sgcg Coding Sequence To test the function of mini-Sgcg in mice, transgenic mice expressing murine mini-Sgcg were generated using the desmin promoter which expresses in both heart and muscle cells [Pacak et al., Genet Vaccines Ther 6: 13 (2008)]. γ-sarcoglycan is required for proper function of both heart and skeletal muscle [Zhu et al., FASEB J 16: 1096-1098 (2002)]. To assess the rescue efficiency of γ-sarcoglycan sub-domains in both muscle tissues, the human desmin promoter is used. Desmin is an intermediate filament that is expressed in all muscle tissue, including heart and skeletal muscle [Su et al., Proc Natl Acad Sci USA 101: 6062-6067 (2004)]. Besides being tissue specific, the desmin gene also becomes activated during muscle differentiation at around the same time as the sarcoglycans [Li et al., J Cell Biol 124: 827-841 (1994); Noguchi et al., Eur J Biochem 267: 640-648 (2000)]. Desmin expression level remains low in dividing myoblasts and reaches a persistently high level in terminally differentiated myofibers. Minimal sequences of the regulatory region of the human desmin gene have been cloned and have been shown to promote high-level target gene expression specifically in both heart and skeletal muscle [Pacak et al., Genet Vaccines Ther 6: 13 (2008)].

Figure 7:
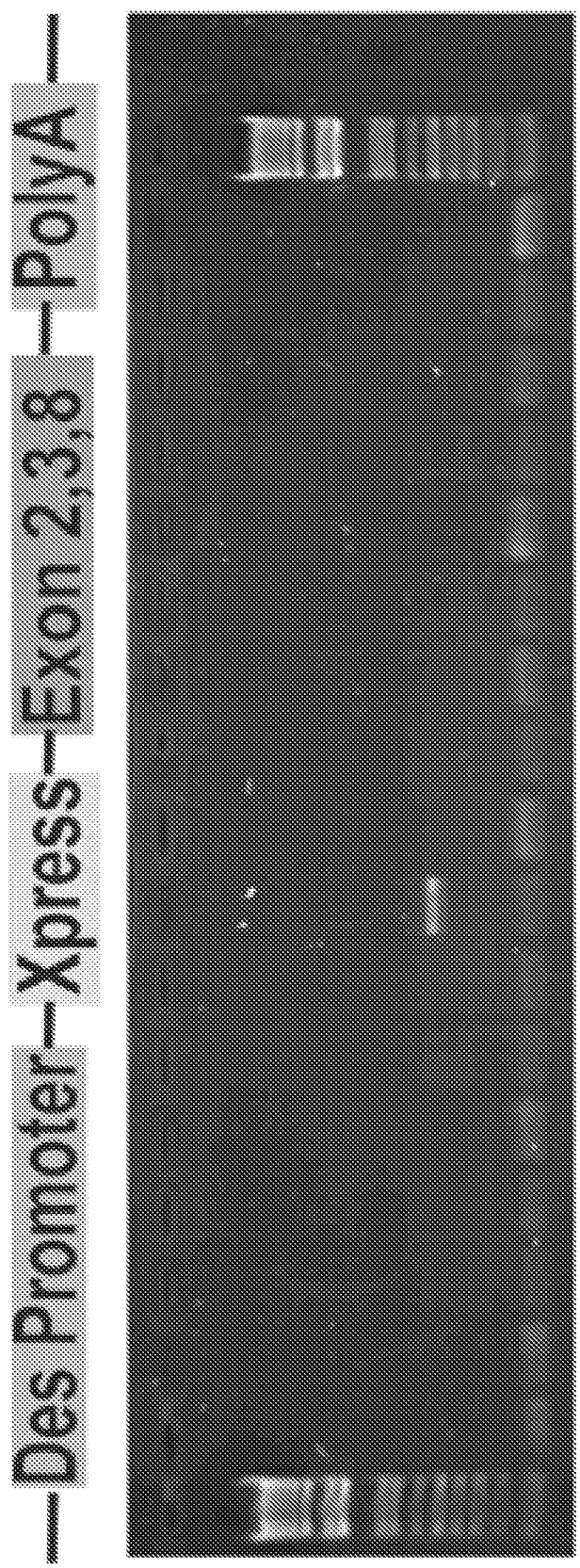
FIG. 7 shows the construct to produce mini-Sgcg in mice. A positive transgenic founder mouse (#23, called "MJ") is indicated.
Figure 8:
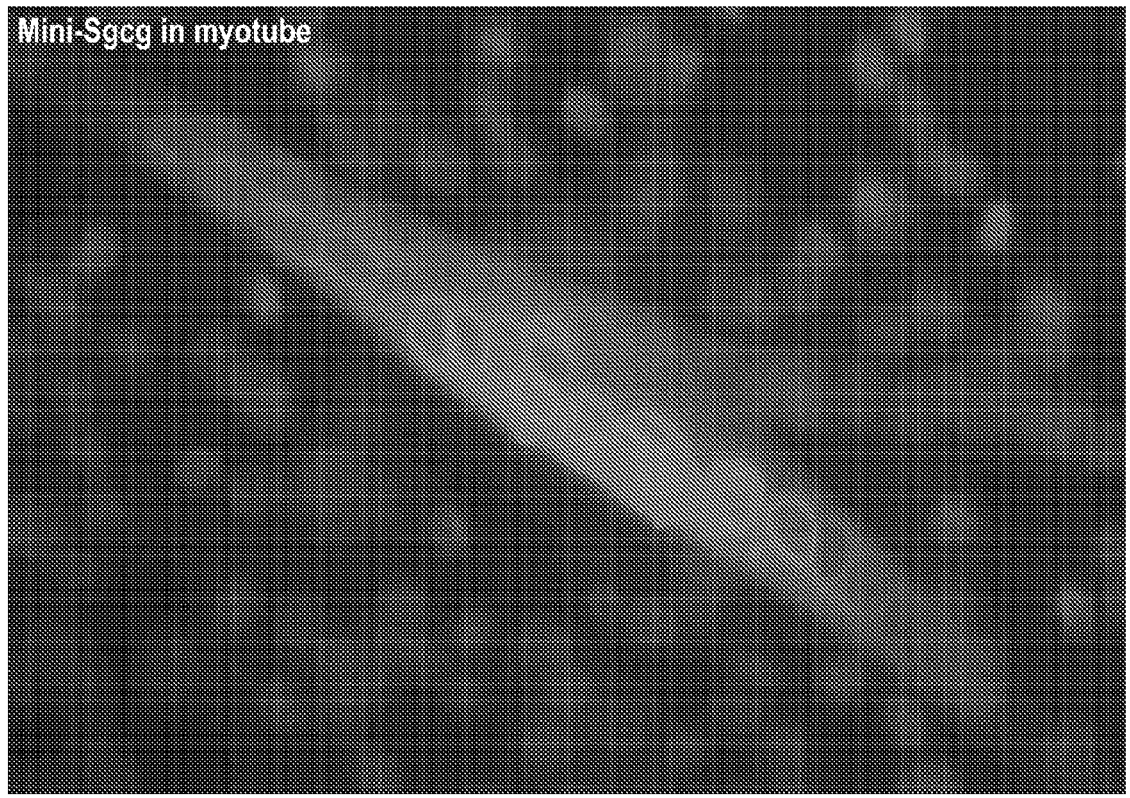
FIG. 8 shows that mini-Sgcg protein is produced in cultured myotubes when transfected with the Des-mini-Sgcg vector and localizes to the muscle membrane.

Using a CMV-mini-Sgcg construct in a pcDNA™ 3.0 vector (Invitrogen), the CMV promoter was replaced with the desmin promoter. An Xpress epitope tag was inserted at the N-terminus of mini-Sgcg. The purified desmin-mini-Sgcg construct (see FIG. 3B) was injected, and a transgene-positive male founder (FIG. 7) was generated. The male founder is being bred to Sgcg$^{-/-}$ mice. Transgene injections continued and five additional founder lines were generated. To test the function of the desmin promoter, C2C12 cells (a cultured muscle cell line) were transfected with the desmin-mini-Sgcg construct, and it was found that mini-Sgcg was produced in differentiated myotubes (FIG. 8).

Level of Expression and Subcellular Localization of Mini-Sgcg Using the Epitope Tag Overexpression of γ-sarcoglycan has been shown to cause severe muscular dystrophy in wild-type mice when expression levels are approximately 20-fold over normal levels [Zhu et al., FASEB J 16: 1096-8 (2002)]. This result was likely due to the formation of abnormal cytoplasmic protein aggregates that interfere with sarcoglycan complex assembly and membrane targeting. The copy number of the currently generated single transgene line appears low, so problems resulting from overexpression are not anticipated. Muscle from desmin-mini-Sgcg transgenic mice are examined for normal membrane localization using the Xpress tag. Experiments have been conducted with this same construct in C2C12 cells, a muscle cell line. In these cells, mini-Sgcg showed similar localization to endogenous γ-sarcoglycan protein.

To further determine the level of mini-Sgcg production, both heart and skeletal muscle tissue from various transgenic lines are collected and processed for immunoblotting experiments. The Xpress epitope tag allows the mini-Sgcg protein to be easily detected on the immunoblot through the use of an antibody against Xpress. Full-length γ-sarcoglycan is detected using NCL-g-sarc antibody (Novocastra). Because this monoclonal antibody is raised against a 12-amino-acid peptide within exon 6, only full-length but not mini-Sgcg protein will be detected. Polyclonal antibodies have also been generated that will recognize both full-length and mini-Sgcg. Following generation of additional transgenic lines, a line is chosen that shows an expression level near wild-type.

Rescue of γ-Sarcoglycan Mutants by Crossing the Transgene into Sgcg$^{-/-}$ Mice To determine if mini-Sgcg can replace full-length Sgcg in mammals, mini-Sgcg Tg$^+$ (transgene positive) mice are bred to Sgcg$^{-/-}$ mice to determine whether heart and muscle dysfunction in Sgcg$^{-/-}$ can be rescued. To prevent phenotypic drift, Sgcg$^{-/-}$ mice are kept as heterozygotes to reduce selection of spontaneously developed modifiers. To introduce the mini-Sgcg transgene into Sgcg$^{-/-}$ mice, Sgcg$^{-/+}$ are bred to mini-Sgcg Tg$^+$ mice. The Tg$^+$ Sgcg$^{-/+}$ F1 males are bred to females. In F2, Tg$^+$ Sgcg$^{-/-}$ mice are produced. Among the littermates, Tg$^+$ wild-type mice are used as positive controls while Tg$^-$ Sgcg$^{-/-}$ mice are used as negative controls. To measure whether mini-Sgcg can improve the impaired muscle function in Sgcg$^{-/-}$ mice, the following aspects are compared between cohorts: subcellular localization of sarcoglycan proteins, direct interaction between mini-Sgcg and other sarcoglycans, plasma membrane permeability of muscle cells, fibrotic tissue deposition (fibrosis) and skeletal muscle function and heart function. Histopathology is examined from transgene-rescued mice to compare to Sgcg$^{-/-}$ and wild-type mice. Muscles are examined for variation in fiber size, central nucleation and replacement by fibrosis and fat. Sgcg$^{-/-}$ and transgenic mice are all on the C57B16/J background.

Subcellular Localization

In heart and muscle cells lacking γ-sarcoglycan, α-, β-, and δ-sarcoglycans are also greatly reduced from muscle membrane while their mRNA levels remain normal, indicating that the presence of γ-sarcoglycan is required for the stable membrane localization of other sarcoglycans in the complex [Hack et al., J Cell Sci. 113(14): 2535-44 (2000)]. To test if the mini-Sgcg protein can restore the proper localization of other sarcoglycans in the absence of full-length γ-sarcoglycan, sections of frozen muscle tissue from Tg$^+$ Sgcg$^{-/-}$ animals are examined and immunofluorescence microscopy is performed using antibodies against α-, β-, and δ-sarcoglycan, respectively. All antibodies are available commercially or are those that were previously generated.

Interaction

In wild-type muscle cells, α-, β-, γ- and δ-sarcoglycans form a tight complex that localizes at the plasma membrane. γ-sarcoglycan can be co-immunoprecipitated (co-IP) with β-sarcoglycan from muscle tissue [Hack et al., J Cell Sci. 113(14): 2535-44 (2000)]. To examine if mini-Sgcg can also interact with β-sarcoglycan, co-IP is performed on protein preparations collected from Tg$^+$ Sgcg$^{-/-}$ mice. The muscle is fractionated to isolate the membranes from the myofibrillar components. These microsomal preparations are performed on whole muscle and only the microsomal fraction is used in the co-IP.

Membrane Permeability

In Sgcg$^{-/-}$ animals, the muscle plasma membrane is weakened and becomes more permeable to large protein molecules. Evans Blue Dye (EBD) is a small molecule dye that binds tightly to albumin and measures sarcolemmal permeability [Matsuda et al., J Biochem 118: 959-64 (1995)]. Mice are injected with EBD and sacrificed 40 hours after injection. EBD is measured by incubating tissues in 1 milliliter of formamide at 55° C. for 2.5 hours and determining the absorbance of the resulting elution at 620 nm. Serum creatine kinase (CK) level is also measured using the EnzyChrom™ Creatine Kinase Assay Kit (BioAssay Systems).

Fibrosis

Collagen is the main component of the excessive fibrous tissue. To quantify collagen deposition, hydroxyproline assays (HOP) are performed to quantitate collagen content. Hydroxyproline is a modified amino acid that comprises a major portion of collagen. Heart and muscle tissues are collected and HOP assays are performed according to described methods [Heydemann et al., Neuromuscul Disord 15: 601-9 (2005)], incorporated herein by reference.

Heart Function

Heart dysfunction is a major direct cause of disability and death in muscular dystrophy patients. Mice lacking γ-sarcoglycans also develop dilated cardiomyopathy. To investigate heart function, echocardiography (ECHO) is performed to measure end-diastolic dimension (EDD), end-systolic dimension (ESD) and fractional shortening (FS).

Analysis of Mice

Mice are analyzed at 12 and 24 weeks of age since these time points display both muscle and heart disease. The numbers used will reflect the physiological studies being conducted and typically require cohorts of between 5 and 10 to show significance (t-test). Additional animals are also used to provide a supply of tissue for microscopy and Western blotting.

| Strain | Ages | Number | Purpose |
| --- | --- | --- | --- |
| C57B16/J | 12 & 24 wks | 10-20 | Tissue, echo, histo, IF |
| Des-mini-Sgcg Tg | 12 & 24 wks | 10-20 | Tissue, echo, histo, IF |
| Sgcg$^{-/-}$ | 12 & 24 wks | 10-20 | Tissue, echo, histo, IF |
| Des-mini-Sgcg Tg/Sgcg | 12 & 24 wks | 10-20 | Tissue, echo, histo, IF |

Mice are being used because they provide a good model of muscle and heart disease that reflects what is seen in humans with similar gene mutations. Over 500 mice of this genotype (Sgcg) have been examined and quantitative methods of phenotyping have been established [Heydemann et al., Neuromuscul Disord 15(9-10): 601-9 (2005); Heydemann et al., J. Clin. Invest 119(12): 3703-12 (2009); Swaggart et al., Physiol Genomics 43(1): 24-31 (2011)]. Given the difference in phenotype expected from the *Drosophila* studies, it is anticipated that cohorts of 5-10 mice will be sufficient.

Expected Results

Several lines of mice harboring des-mini-Sgcg transgenes that express mini-Sgcg protein at different levels in muscle tissue are expected, with some lines at near-endogenous γ-sarcoglycan levels. It is expected that mini-Sgcg is undetectable in other tissues. It is also expected that mini-Sgcg protein is enriched at the plasma membrane in wild-type mice. It is possible that some cytoplasmic or perinuclear staining of mini-Sgcg is observed because the presence of full-length Sgcg may compete with mini-Sgcg for inclusion in the sarcoglycan complex. More distinct plasma membrane staining of mini-Sgcg in Sgcg$^{-/-}$ mice is expected. A similar pattern of expression has been seen in studies in *Drosophila*. In Tg$^+$ Sgcg$^{-/-}$ muscle, it is expected that mini-Sgcg expression will restore the membrane localization of other sarcoglycans. Mini-Sgcg is also expected to be present among the proteins associated with, and pulled down by, β-sarcoglycan. Improved histopathology, reduced EBD uptake, decreased CK level, less HOP and improved heart function are expected in Tg$^+$ Sgcg$^{-/-}$ compared to Tg$^-$ Sgcg$^{-/-}$ littermates without the transgene. These would all represent an improvement in muscle and heart disease, establishing that mini-Sgcg rescues the Sgcg mutation, as expected.

Based on the *Drosophila* studies described herein, mini-Sgcg is expected to have many of the functions of Sgcg. The transgenic mice will also allow for the investigation of the interaction with other important components of the dystrophin complex, such as dystrophin, sarcospan, and interactions with other transmembrane components.

For exon skipping, fibroblasts have been obtained from human LGMD2C patients. A forced MyoD expression approach, described below, is used to induce these cells into a myogenic lineage [Kimura et al., Hum Mol Genet 17: 2507-17 (2008)]. These cells will provide a cell-based environment in which to test human Sgcg exon skipping.

Example 3

Exon Skipping in Muscle Culture Derived from Human Patients

The rationale for the experiments described below is that exon skipping requires optimization of antisense polynucleotides and proof-of-function in vitro.

Use MyoD Transformation to Induce Cultured Primary Human Fibroblasts to Become Myoblasts Fibroblasts isolated from two LGMD2C patients carrying a deletion of exon 6 in the Sgcg gene have been obtained. MyoD is a master regulator of the muscle differentiation program. Forced expression of MyoD in fibroblasts can convert the fibroblasts to a muscle lineage [Lattanzi et al., J Clin Invest 101: 2119-2128 (1998)].

MyoD is a key initiator of the skeletal muscle differentiation program [Weintraub et al., Science 251: 761-766 (1991)]. MyoD is responsible for activating other essential muscle regulators, such as myocyte enhancer factor-2 (MEF2) and myogenin. It has been shown that forced expression of MyoD in fibroblasts is able to convert fibroblasts to myoblasts both in vitro and in vivo [Kimura et al., Hum Mol Genet 17: 2507-2517 (2008)]. Therefore, introducing MyoD into fibroblasts is sufficient to convert a fibroblast down a myoblast lineage. Once established, myoblasts under the proper conditions can be induced to differentiate further into myotubes. This process is applied to human fibroblasts and "MyoD forced fibroblasts" are useful for diagnosing human muscle disease. Myoblasts derived from human patients bearing the γ-sarcoglycan mutation described herein are required in order to test the efficiency of exon skipping induced by different potential AONs. Using dermal fibroblasts from LGMD2C patients avoids the need for painful muscle biopsies required to obtain myoblasts.

Kimura et al. made a tamoxifen-inducible MyoD construct and inserted the MyoD gene into fibroblast genomes via lentiviral vector. They found that the transfected fibroblasts were able to form myotubes both in vivo and in vitro upon administration of tamoxifen. The MyoD vector is used to transfect the fibroblasts obtained from the LGMD2C patients. The transfected fibroblasts are expanded without tamoxifen induction and frozen in small aliquots for future use.

MyoD Forced Fibroblasts Treated with Antisense Polynucleotides Induce Exon Skipping of Exons 4-7 of Sgcg To target specific exons, antisense polynucleotides (AONs) are designed to block splice donor, splice acceptor or exonic splicing enhancer (ESE) sites. Splice donor and splice acceptor sites localize at exon-intron boundaries and have highly conserved sequences. Based on nucleotide sequence and secondary structure of RNA transcripts, ESE sites are predicted at high accuracy by software such as ESEfinder, which predicts binding sites for the four most abundant serine/arginine-rich proteins involved in splicing regulation (SR proteins). A series of AONs are designed based on the prediction of available software programs. The efficiency and specificity of different AONs in myotubes converted from patient fibroblasts is then examined, following a protocol that has been used to test exon skipping efficiency in primary human myotubes [Aartsma-Rus et al., Hum Mol Genet 12: 907-914 (2003)]. Specifically, fibroblasts are treated with tamoxifen for 24 hours to induce MyoD expression before switching the fibroblasts to differentiation medium for induction of myotube formation. Following 7-14 days of serum deprivation, the myotubes are transfected with AON using polyethylenimine (PEI) for 3 hours in low-serum medium. At 24 hours post-transfection, total RNA is extracted from the myotube cultures. The ratio of the shorter mRNA transcript composed of only exon 1, 2, 3 and 8 to the full-length transcripts is quantified by performing reverse transcriptase-polymerase chain reaction (RT-PCR). The PCR product is fractionated on an agarose gel and the ratio of short/long products is calculated using Photoshop software. The AONs with highest exon skipping efficiency are selected.

Use of Immunofluorescence (IF) Microscopy to Test Whether the Carboxy-Terminus of γ-Sarcoglycan is Present after Anti-Sense Treatment, and Whether Other Sarcoglycans are Stabilized Using this Approach Frame shift mutations in the Sgcg gene in patients result in a prematurely terminated protein without a C-terminus. Previous study has also shown that the protein product of the Sgcg gene with a 525ΔT mutation was not detected by a rabbit polyclonal antibody raised again the entire Sgcg protein [McNally et al., Am J Hum Genet 59: 1040-1047 (1996)]. This result suggested that the mutant Sgcg gene was not able to produce a stable protein product. This is also likely to be the case in the LGMD2C patients from whom the fibroblasts were obtained.

Restoration of the reading frame results in translation of an internally truncated protein with a normal C-terminus. To visualize the production of AON-induced protein, IF microscopy is performed using the polyclonal antibody against the full-length γ-sarcoglycan protein on myotubes with and without AON treatment. By using IF, it can also be determined whether the smaller γ-sarcoglycan protein localizes to the membrane. IF is also performed to detect other sarcoglycans (e.g., α-, β- and δ-sarcoglycan) and assess whether they have been restored to the membrane in $Tg^+$ $Sgcg^{-/-}$ mice.

Expected Results

It is expected that fibroblasts are converted to myoblast-like cells that are capable of forming myotubes upon tamoxifen administration. Alternatively, myoblasts are obtained from human patients. It is expected that several AON treatments will convert a substantial fraction of full-length Sgcg transcript to smaller, internally truncated protein. It is expected that no Sgcg staining is detected by the polyclonal antibody in patient myotubes without AON treatment, while the internally truncated γ-sarcoglycan protein is expected to be localized at the membrane of a substantial percentage of treated myotubes. Further, it is expected that other components of the dystrophin complex are restored at the plasma membrane of the myotubes that show positive γ-sarcoglycan membrane staining. In the event that the polyclonal antibody is able to detect residual product of the 525ΔT Sgcg gene, an antibody against the C-terminus of the γ-sarcoglycan protein is raised to specifically detect the truncated γ-sarcoglycan protein.

Example 4

Walking Behavior in Sgcd Null Flies

This experiment was designed to test whether loss of Sgcd in *Drosophila* negatively affects their walking activity.

Figure 9:
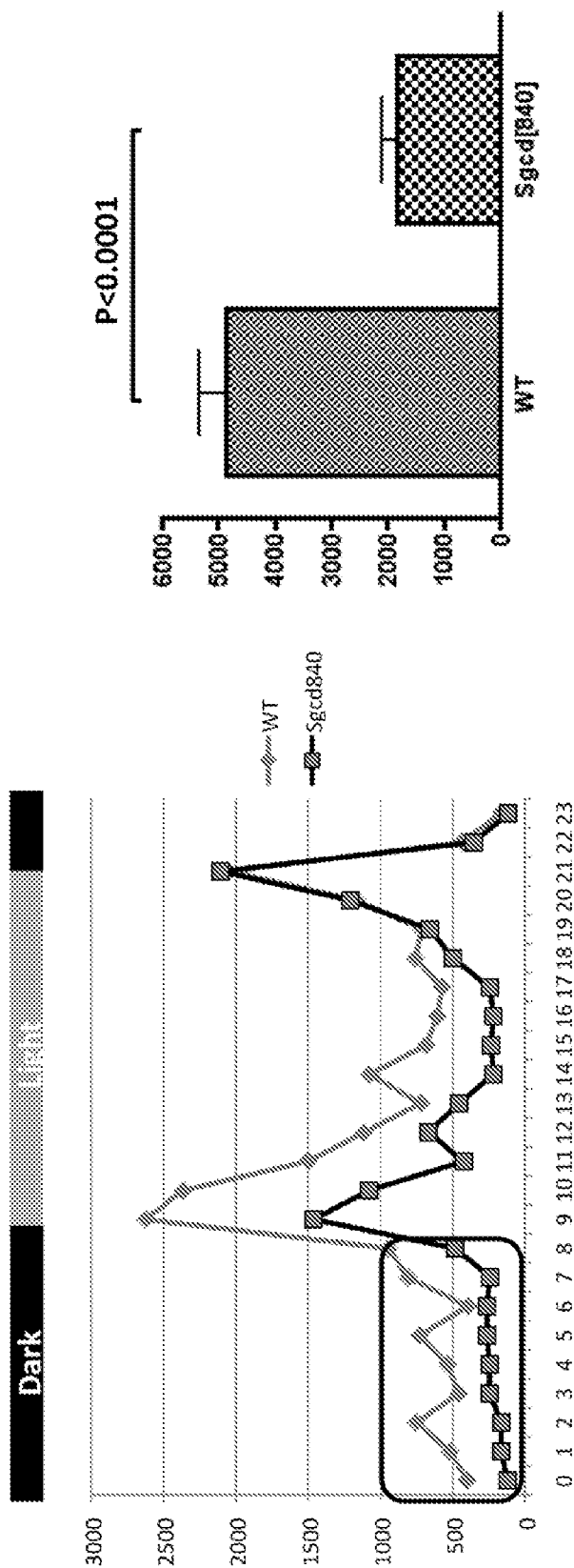
FIG. 9 depicts the rescue of walking ability in Sgcd null flies using mini-Sgcg. On the left panel, the Y axis is number of beam breaks per hour, and the X axis is hour where midnight is designated as 0. On the right panel, the Y axis is total number of beam breaks from midnight to 8 AM.

A monitor designed to test walking activity (Trikinetics, Waltham, Mass.) was used to record movement, measured as infrared beam breaks, over a 24 hour period on individual *Drosophila*. Normally *Drosophila* display a marked spike in activity at dawn and dusk, irrespective of genotype. The data are shown in FIG. 9. To assess basal activity, data was analyzed from midnight to 8 AM, boxed as region of interest in left panel of FIG. 9. Wildtype flies have significantly more activity, measured as infrared beam breaks, than $Sgcd^{840}$ flies which lack γ-sarcoglycan and serve as a model for Limb Girdle Muscular Dystrophy type 2C. This decline in activity mirrors what is seen in muscular dystrophy patients who display reduced ambulation due to muscle weakness.

Figure 10:
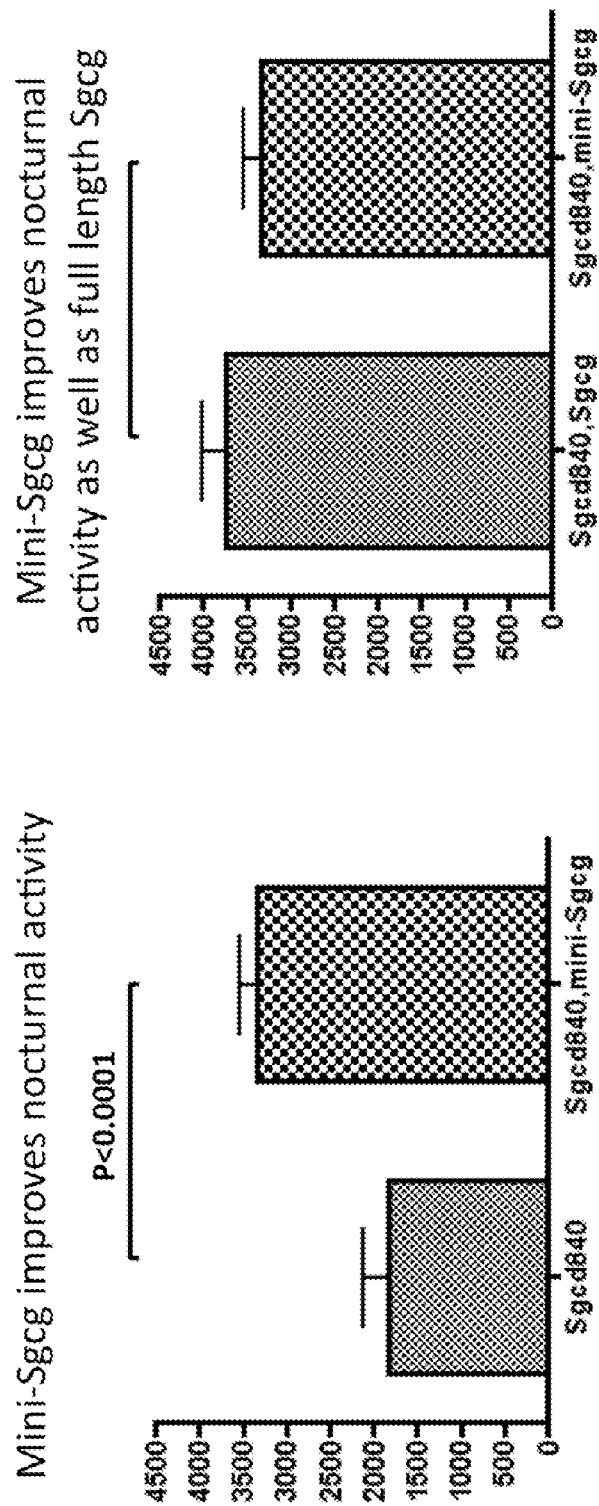
FIG. 10 shows that expression of mini-Sgcg in Sgcd$^{840}$ flies significantly improved nocturnal activity.

Expression of Mini-Sgcg in $Sgcd^{840}$ Flies Significantly Improved Nocturnal Activity FIG. 10 shows that expression of mini-Sgcg in $Sgcd^{840}$ flies significantly improved nocturnal activity of mutant *Drosophila*, measured as infrared beam breaks (compare $Sgcd^{840}$ vs $Scgd^{840}$ mini-Sgcg in left panel). These data indicate that mini-Sgcg can function in the place of full length γ/δ-sarcoglycan which is deleted in $Sgcd^{840}$ flies. The right hand panel shows that nocturnal activity was equally rescued by Sgcg, which is the full length mouse γ-sarcoglycan protein, and mini Sgcg ($Sgcg^{840}$, Sgcg compared to $Sgcd^{840}$, mini-Sgcg). These data indicate that mini-Sgcg is as functional as full length Sgcg for restoring walking activity.

Example 5

Mini-Sgcg Protein is Stably Produced in Mammalian Skeletal Muscle and Heart

Figure 11:
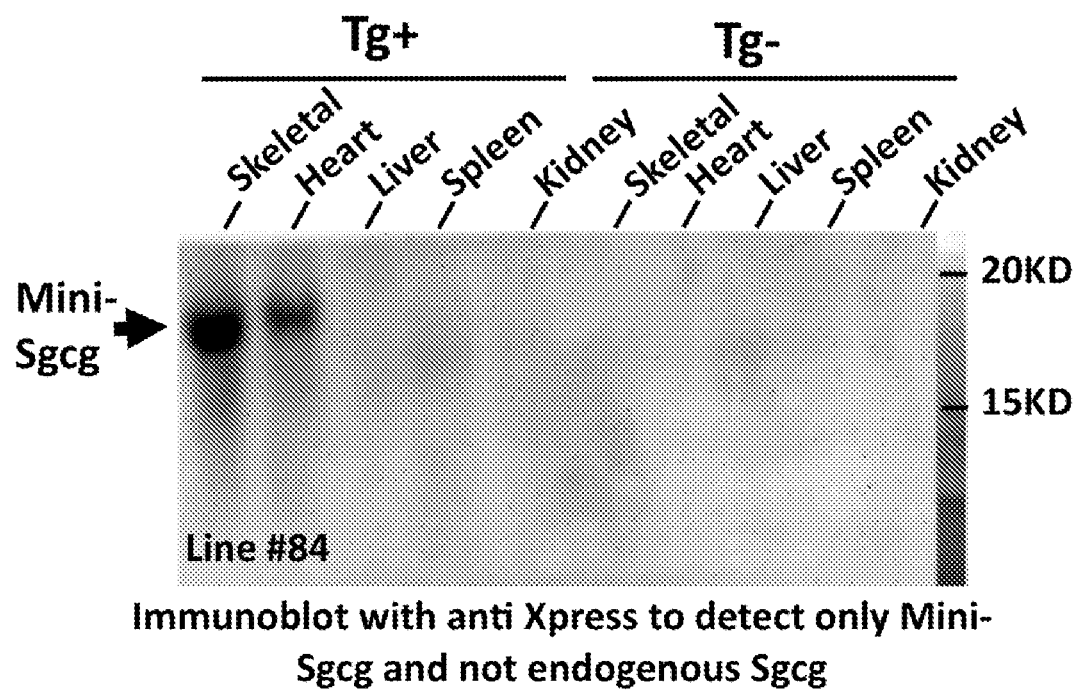
FIG. 11 shows that mini-Sgcg protein can be stably produced in mammalian skeletal muscle (skeletal) and heart (Heart).

A transgene using the desmin promoter to drive expression of Mini-Sgcg was introduced in normal wildtype mice (Tg+). The data are presented in FIG. 11. Skeletal (quadriceps) muscle isolation and immunoblotting was performed as described in Hack et al. [J Cell Sci. 113: 2535-44 (2000)]. Mini-Sgcg protein is robustly detected in skeletal muscle and heart at the expected molecular weight of 18 KDa (FIG. 11, arrow). It is not detected in other cell types such as liver, spleen and kidney. This expression pattern reflects the desmin promoter which drives expression only in heart and muscle. Mini-Sgcg is not detected in wildtype, non-transgenic mice (Tg−) (see FIG. 11). The Xpress epitope (Invitrogen) was placed on Mini-Sgcg, and an affinity purified polyclonal rabbit antibody raised to the Xpress epitope was used at a 1:1000 dilution to detect expression from the transgene. These data demonstrate that mini-Sgcg protein is stable in mammalian muscle and heart, and further that the protein is able to correctly translocate to the muscle membrane.

Characterization of Transgenic Mice

Figure 12:
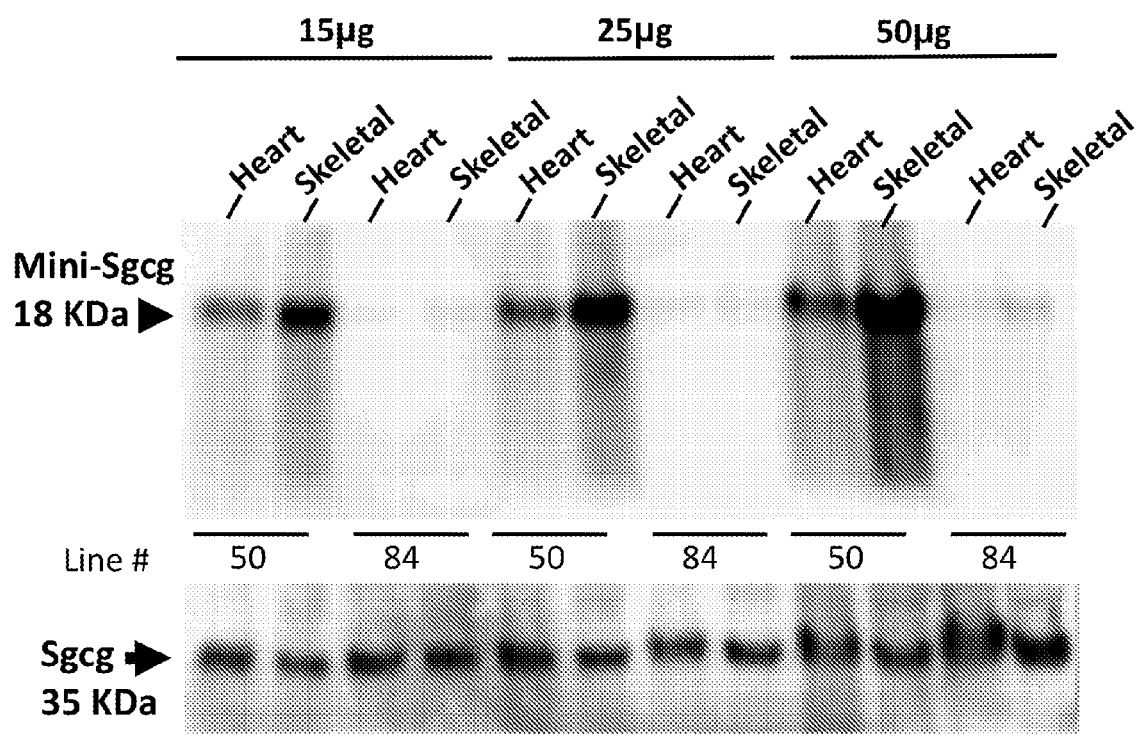
FIG. 12 depicts mini-Sgcg expression in two different transgenic lines. The upper panel shows expression at three different concentrations from transgenic line 50 or transgenic line 84.

Two different transgenic lines were established expressing mini-Sgcg. The transgenic animals were created using standard protocols. As depicted in FIG. 12, line 50 expresses at higher levels than line 84. The upper panel of FIG. 12 shows expression at three different concentrations from line 50 or line 84. These data demonstrate that mini-Sgcg is a stable protein in skeletal muscle and cardiac muscle. An antibody to endogenous γ-sarcoglycan protein was used to demonstrate expression of Sgcg protein (full length) in these same samples. A polyclonal affinity purified rabbit anti-Xpress was generated at Pocono Rabbit Farms. It was used at a dilution of 1:1000 for immunoblotting to detect mini-Sgcg (FIG. 12, upper panels). The antibody to γ-sarcoglycan was previously described [McNally et al., Hum Mol Genet. 5: 1841-7 (1996)] and was used to detect endogenous γ-sarcoglycan at 1:1000.

Mini-Sgcg Protein Localizes to the Plasma Membrane of Skeletal Muscle

Figure 13:
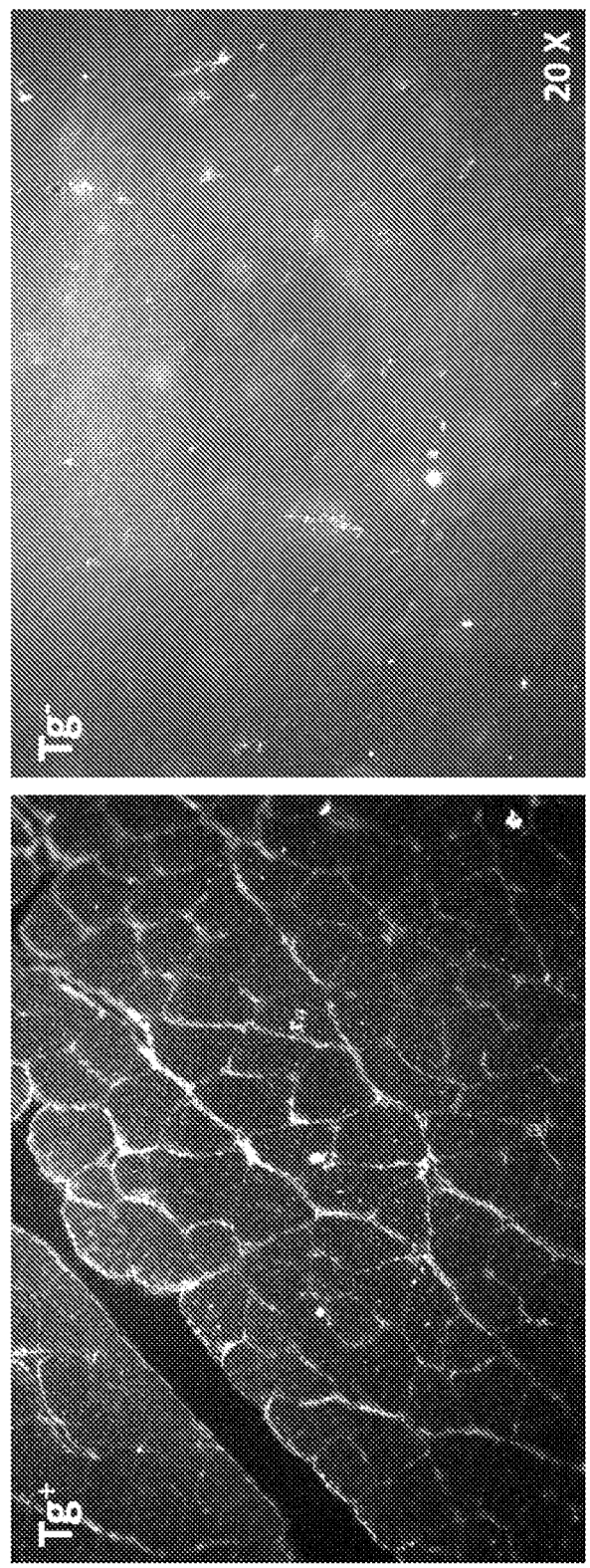
FIG. 13 depicts that mini-Sgcg protein localizes to the plasma membrane of skeletal muscle when expressed in wildtype normal mice (Tg$^+$). This same signal was not detected in transgenic negative (Tg$^-$) muscle demonstrating that this signal derives from the transgene.

FIG. 13 shows that mini-Sgcg protein localizes to the plasma membrane of skeletal muscle when expressed in wildtype normal mice (Tg+). An anti-Xpress antibody was used to detect expression at the periphery of each myofiber consistent with localization at the plasma membrane, or sarcolemma, of skeletal muscle. This intracellular pattern is identical to normal γ-sarcoglycan (Sgcg) protein, and indicates that mini-Sgcg translocates properly. This same signal was not detected in transgenic negative (Tg−) muscle (FIG. 13, right panel) demonstrating that this signal derives from the transgene. Immunostaining was performed as described in Hack et al. [J Cell Sci. 113: 2535-44 (2000)]. The affinity purified polyclonal antibody to the Xpress epitope was used at 1:200.

Figure 14:
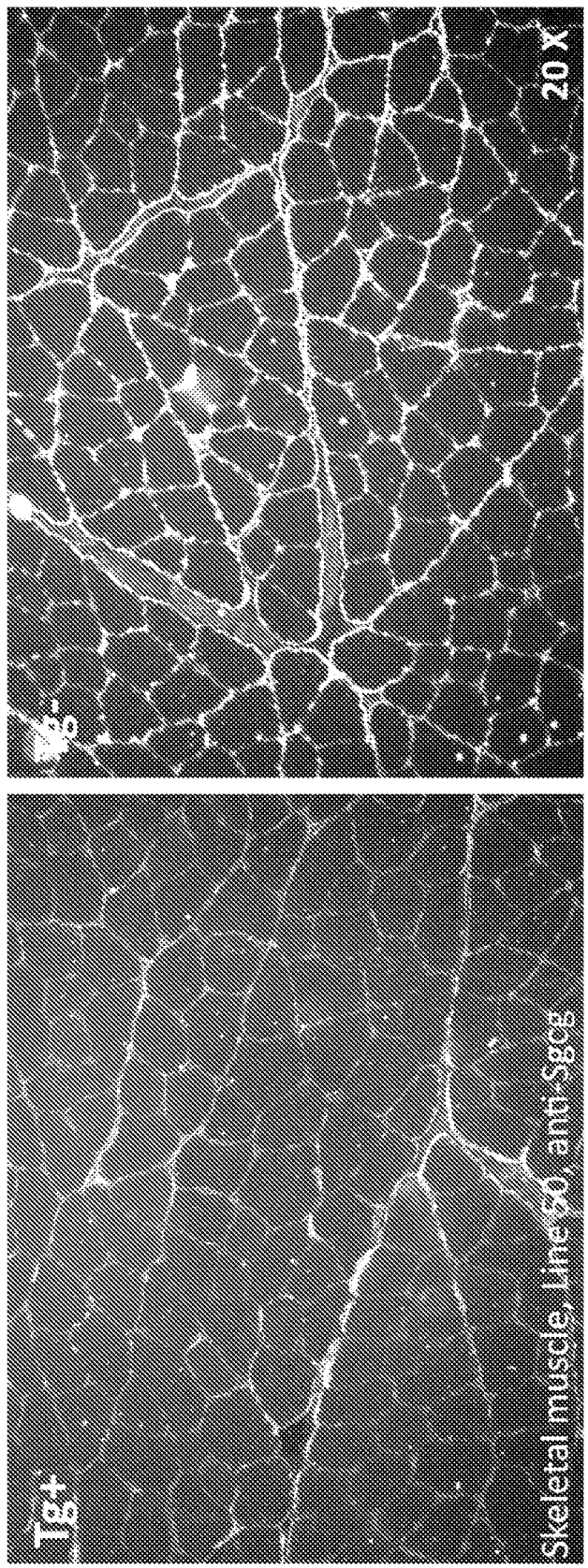
FIG. 14 shows that expression of full length endogenous γ-sarcoglycan protein (Sgcg) is diminished at the plasma membrane when mini-Sgcg is present (Tg$^+$ left panel) versus when mini-Sgcg is absent (Tg$^-$ right panel)).

Expression of Full Length Endogenous γ-Sarcoglycan Protein is Diminished at the Plasma Membrane when Mini-Sgcg is Present FIG. 14 shows the results of an experiment designed to test whether the mini-Sgcg protein can compete with the endogenous γ-sarcoglycan protein in vivo. Note that the signal intensity for full length endogenous Sgcg is reduced in the left panel of FIG. 14 compared to the right panel. These data demonstrate that mini-Sgcg competes with endogenous normal Sgcg and therefore mini-Sgcg can replace full length Sgcg. Immunostaining was performed as described in Hack et al. [J Cell Sci. 113: 2535-44 (2000)]. The polyclonal anti-γ-sarcoglycan antibody was used at 1:200.

Figure 15:
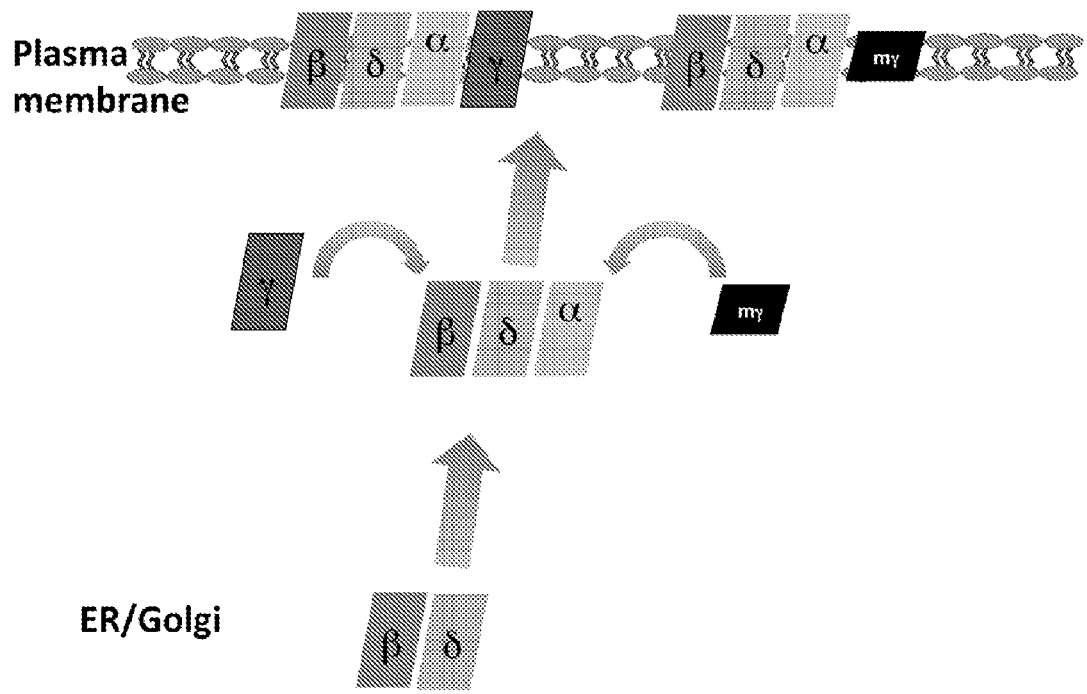
FIG. 15 depicts a model for sarcoglycan assembly.

FIG. 15 depicts a model for sarcoglycan assembly. Published literature describes the assembly of the sarcoglycan complex [Chan et al., J Cell Biol. 143: 2033-44 (1998); Chen et al., Exp Cell Res. 312: 1610-25 (2006); Hack et al., J Cell Sci. 113: 2535-44 (2000)]. In mammalian muscle, where there are four sarcoglycan subunits, α-, β-, γ-, and δ-sarcoglycan, the β-sarcoglycan and δ-sarcoglycan subunits assemble first as a unit in the endoplasmic reticulum (ER)/Golgi apparatus. This step is followed by the addition of α-sarcoglycan and γ-sarcoglycan. The assembly of the sarcoglycan complex is necessary but not sufficient for translocation to the plasma membrane [Chen et al., Exp Cell Res. 312: 1610-25 (2006)]. Mutations in sarcoglycan subunits disrupt normal translation of the sarcoglycan complex from the ER/Golgi to the plasma membrane. Translocation to the plasma membrane requires an interaction with dystrophin and is associated with stabilization of the plasma membrane. Sarcoglycan complexes containing γ-sarcoglycan (γ) or Mini-Sgcg (mγ) successfully translocate to the plasma membrane. In Drosophila muscle, where there is only a single γ/δ-sarcoglycan subunit, mammalian mini-Sgcg can rescue the loss of the single γ/δ-sarcoglycan moiety and rescue defective heart and muscle function (as shown herein).

Mini-Sgcg Enriches in the Heavy Microsomal Fraction of Muscle

Figure 16:
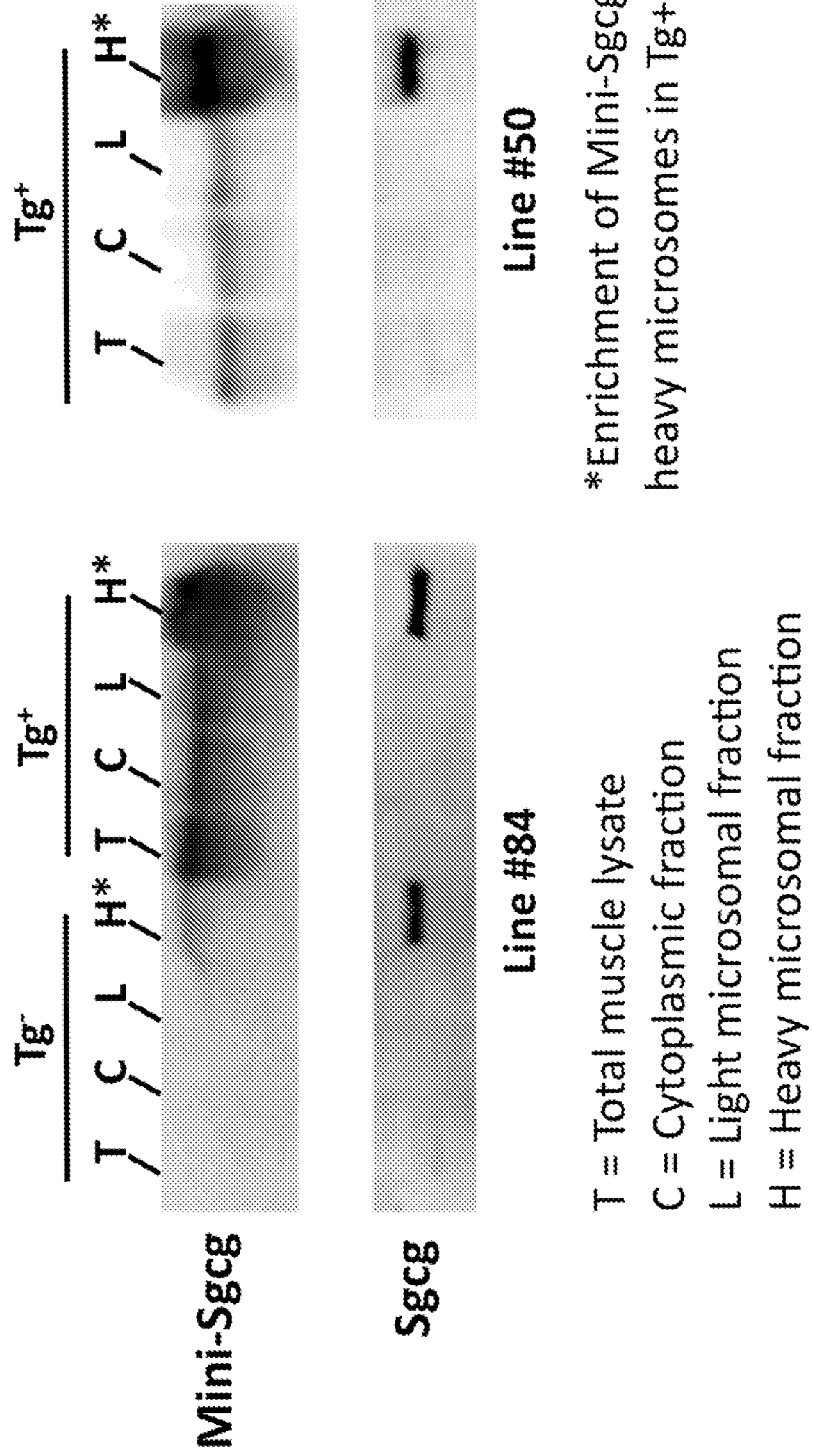
FIG. 16 shows that mini-Sgcg is enriched in the heavy microsomal fraction of muscle.

Muscle can be fractionated into a cytoplasmic (C) and a membrane fraction. The membrane fraction can be further subdivided into light (L) and (H) microsomes. The sarcoglycan complex is normally found in the heavy microsomal complex containing plasma membrane. Muscle from mice expressing mini-Sgcg (T+) was fractionated to separate the cytoplasm from the light and heavy microsomal fractions. The heavy microsomal fraction contains the ER, Golgi and plasma membrane fractions. In the two different transgenic lines (84 and 50), mini-Sgcg enriches greatly in the heavy microsomal fraction (FIG. 16). This demonstrates that mini-Sgcg is found in the proper intracellular fraction. The method for isolating microsomes was as previously described [Ohlendieck et al., J Cell Biol. 112: 135-48 (1991)] with modification described in [Duclos et al., J Cell Biol. 142: 1461-71 (1998); Hack et al., J Cell Sci. 113: 2535-44 (2000)]. The antibody used in the upper panels of FIG. 16 is the affinity purified anti-Xpress epitope. The antibody used in the lower panel of FIG. 16 was a rabbit polyclonal anti-γ-sarcoglycan antibody [McNally et al., Hum Mol Genet. 5: 1841-7 (1996)]. Antibodies were used at 1:500. All secondary antibodies were from Jackson Immunochemicals (goat-anti-rabbit-HRP) used at 1:1000.

Establishment of Human Cell Lines with SGCG Mutations

Figure 17:
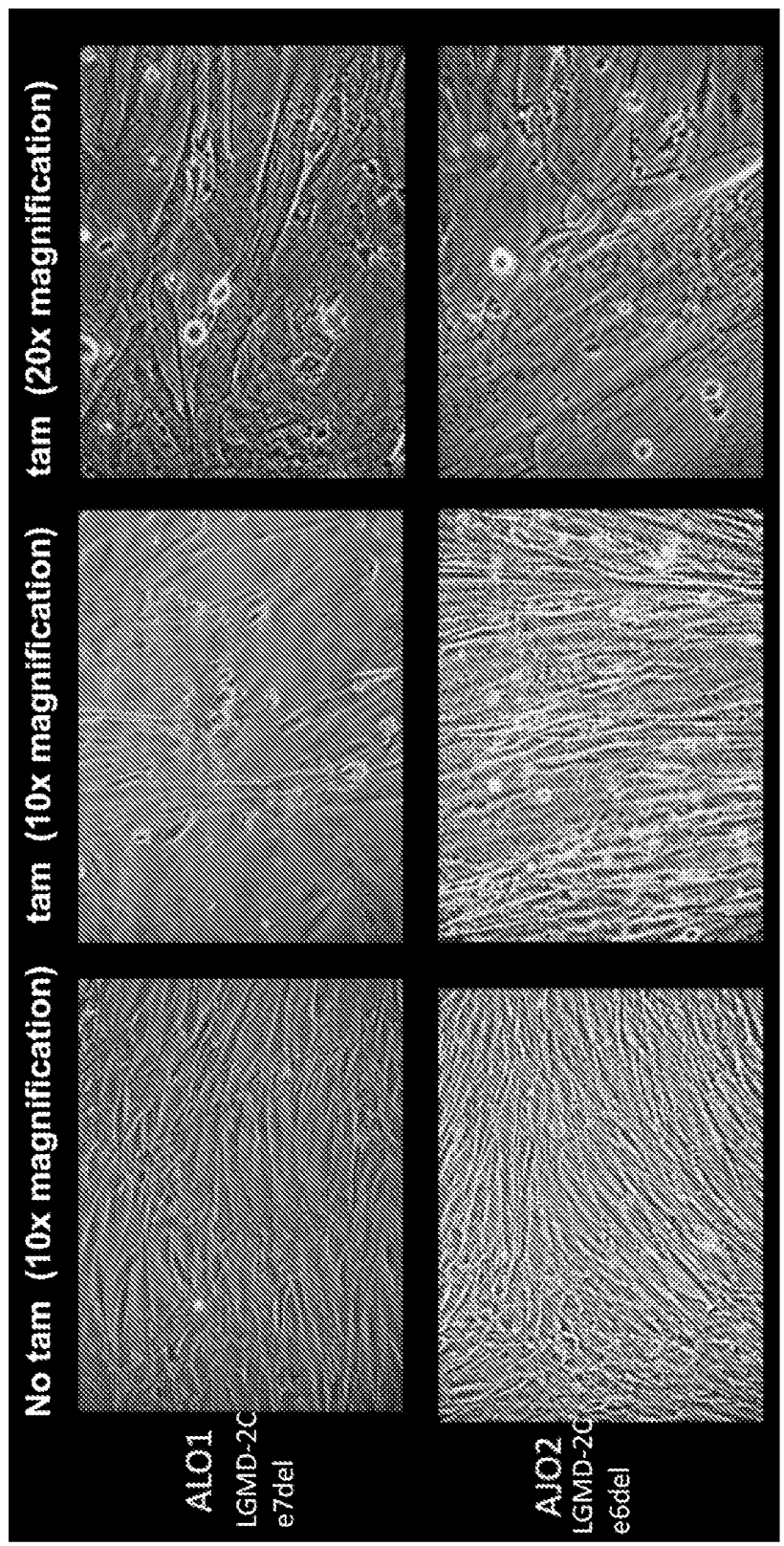
FIG. 17 shows two human cell lines with SGCG mutations that have been infected with retroviruses expressing telomerase and MyoD. The top row is from an LGMD 2C patient whose disease arises from a mutation deleting exon 7 in SGCG. The bottom row is from an LGMD 2C patient who is deleted for exon 6 of SGCG.

Two human cell lines with SGCG mutations have been established for the purposes of testing exon skipping for the production of mini-Sgcg. These lines are derived from dermal fibroblasts isolated from human patients with primary SGCG gene mutations. The top row of FIG. 17 shows cells from an LGMD 2C patient whose disease arises from a mutation deleting exon 7 in SGCG. The bottom row of FIG. 17 shows cells from an LGMD 2C patient who is deleted for exon 6 of SGCG. These cell lines were infected with retroviruses expressing telomerase and MyoD. The infection with the telomerase virus provides an immortalized cell line, and the infection with the MyoD virus provides a regulated means of inducing muscle differentiation since the nuclear position of MyoD is under the control of tamoxifen [Kimura et al., Hum Mol Genet. 17: 2507-17 (2008); Kendall et al., Sci Transl Med. 4: 164ra160 (2012)]. This combination creates cell lines that are immortalized with telomerase, which provides a ready supply of cells. The regulatable control of MyoD nuclear expression provides a mechanism by which muscle conversion can be induced at will. These cell lines serve as cellular models of LGMD 2C, and provide the format in which induced expression of mini-Sgcg can be tested in a human cell context. With the addition of tamoxifen, the MyoD localizes in the nucleus and the cells undergo differentiation into elongated myotubes (FIG. 17, middle and right panel).

LGMD 2C Cell Lines Differentiated into the Muscle Lineage

Figure 18:
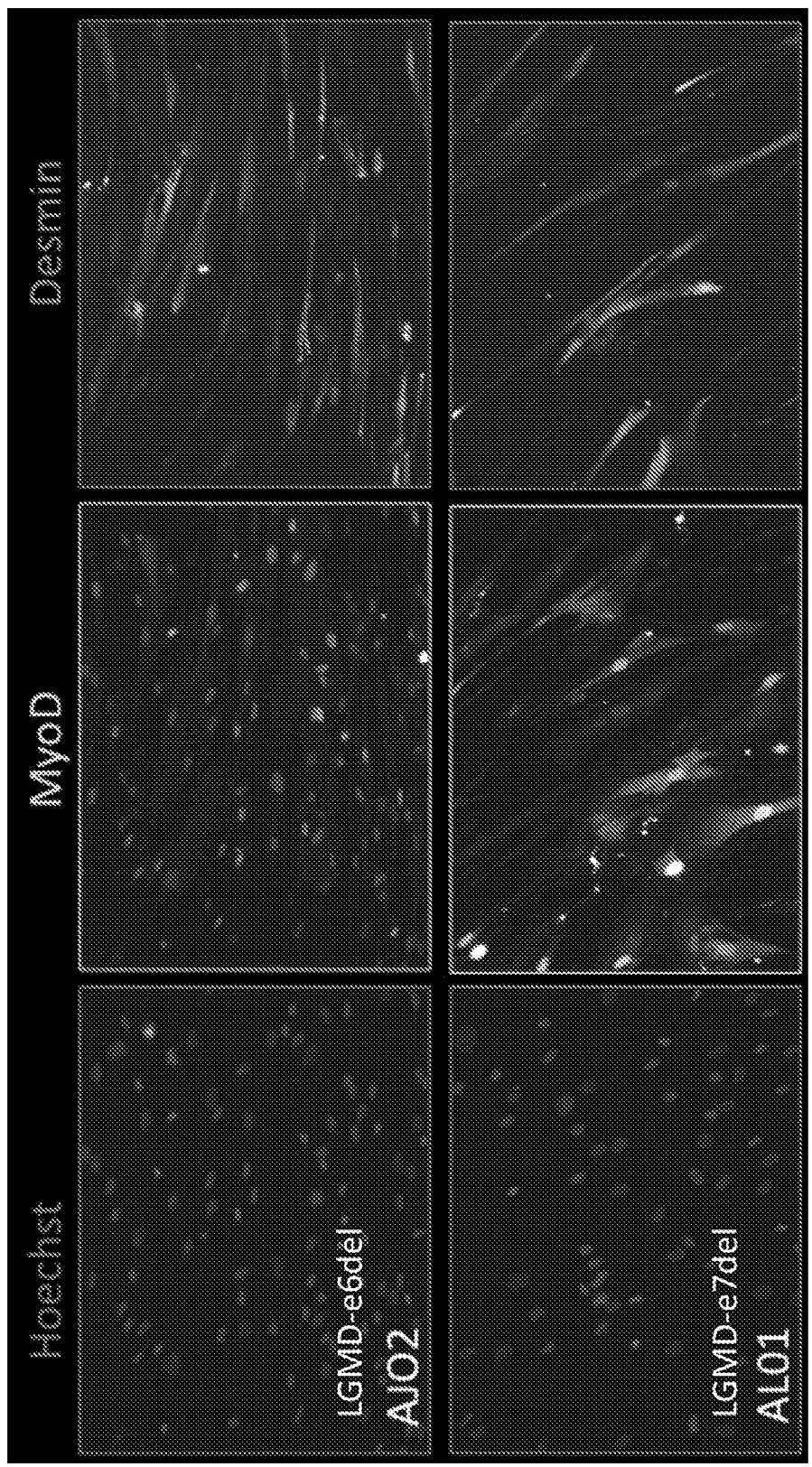
FIG. 18 depicts LGMD 2C cell lines differentiated into the muscle lineage (6 days of differentiation). The top row is from an LGMD 2C patient whose disease arises from a mutation deleting exon 6 in SGCG, and the bottom row is from an LGMD 2C patient who is deleted for exon 7 of SGCG. MyoD, a muscle marker, is expressed from the retrovirus (middle panel) and desmin, a muscle marker, is induced from MyoD (right panel) indicating that these cells are viable models for muscle disease. The left hand panel (Hoechst) shows nuclei.

FIG. 18 shows that LGMD 2C cell lines differentiated into the muscle lineage following 6 days of differentiation. With the addition of tamoxifen, the LGMD 2C cell line lines undergo morphological changes becoming elongated and expressing myogenic markers and demonstrating differentiation into the muscle lineage. MyoD, a muscle marker, is expressed from the retrovirus (FIG. 18, middle panel) and desmin, a muscle marker, is induced from MyoD (FIG. 18, right panel) indicating that these cells are viable models for muscle disease. The left hand panel of FIG. 18 (Hoechst) shows nuclei. Methods for cell culture are described in Kendall et al. [Sci Transl Med. 4: 164ra160 (2012)]. The anti-desmin and anti-MyoD antibodies were from Thermo-Fisher (PA5-17182 and MA1-41017, respectively). Secondary antibodies were from Molecular Probes/Invitrogen (goat-anti mouse Cy3, goat anti mouse Alexa488, respectively).

What is claimed is:

1. A method of inducing exon-skipping of a gamma sarcoglycan RNA, comprising delivering to a human muscle cell an antisense polynucleotide, wherein the polynucleotide is about 5 to about 50 nucleotides in length and specifically hybridizes to an exon target region of a gamma sarcoglycan RNA, wherein the exon is selected from the group consisting of exon 4 (SEQ ID NO: 1), exon 5 (SEQ ID NO: 2), exon 6 (SEQ ID NO: 3), exon 7 (SEQ ID NO: 4) and a combination thereof, thereby inducing exon-skipping of the gamma sarcoglycan RNA.

2. The method of claim 1, wherein the human muscle cell is in a patient who has muscular dystrophy.

3. The method of claim 2, wherein the muscular dystrophy is Limb Girdle Muscular Dystrophy type 2C (LGMD2C).

4. A method of improving muscle function in a patient suffering from Limb Girdle Muscular Dystrophy type 2C (LGMD2C) comprising the step of administering to the patient a therapeutically effective amount of a composition comprising an antisense polynucleotide, wherein the polynucleotide specifically hybridizes to an exon target region of a gamma sarcoglycan RNA, wherein the exon is selected from the group consisting of exon 4 (SEQ ID NO: 1), exon 5 (SEQ ID NO: 2), exon 6 (SEQ ID NO: 3), exon 7 (SEQ ID NO: 4) and a combination thereof, and a physiologically compatible phosphate buffer, thereby improving muscle function.

5. The method of claim 4 wherein the improvement is a cardiac muscle improvement.

6. The method of claim 4 wherein the improvement in muscle function is an improvement in muscle strength.

7. The method of claim 4 wherein the improvement in muscle function is an improvement in motor stability.

8. The method of claim 1, wherein the antisense polynucleotide induces skipping of exon 4 (SEQ ID NO: 1), exon 5 (SEQ ID NO: 2), exon 6 (SEQ ID NO: 3), and exon 7 (SEQ ID NO: 4) of the gamma sarcoglycan RNA.

9. The method of claim 4, wherein the antisense polynucleotide induces skipping of exon 4 (SEQ ID NO: 1), exon 5 (SEQ ID NO: 2), exon 6 (SEQ ID NO: 3), and exon 7 (SEQ ID NO: 4) of the gamma sarcoglycan RNA.

10. The method of claim 1, further comprising delivering to the cell an additional antisense polynucleotide that specifically hybridizes to an exon of a gamma sarcoglycan RNA.

11. The method of claim 4, further comprising delivering to the cell an additional antisense polynucleotide that specifically hybridizes to an exon of a gamma sarcoglycan RNA.

12. The method of claim 1, wherein the delivering is oral or parenteral.

13. The method of claim 12, wherein the parenteral delivering is intravenous, intra-arterial, subcutaneous, intraperitoneal, or intramuscular.

14. The method of claim 13, wherein the delivering is by injection.

15. The method of claim 13, wherein the delivering is by infusion.

16. The method of claim 4, wherein the administering is oral or parenteral.

17. The method of claim 16, wherein the parenteral delivering is intravenous, intra-arterial, subcutaneous, intraperitoneal, or intramuscular.

18. The method of claim 17, wherein the delivering is by injection.

19. The method of claim 17, wherein the delivering is by infusion.

20. A method of inducing exon-skipping of a gamma sarcoglycan RNA, comprising delivering to a cell an antisense polynucleotide that is about 5 to about 50 nucleotides in length and specifically hybridizes to an exon target region of a gamma sarcoglycan RNA to form a duplex, wherein the antisense polynucleotide is 100% complementary to the exon target region within the duplex, and wherein the exon is selected from the group consisting of exon 4 (SEQ ID NO: 1), exon 5 (SEQ ID NO: 2), exon 6 (SEQ ID NO: 3), exon 7 (SEQ ID NO: 4) and a combination thereof, thereby inducing exon-skipping of the gamma sarcoglycan RNA.

21. The method of claim 20, wherein the cell is a human muscle cell.

22. The method of claim 20, wherein the human muscle cell is in a patient who has muscular dystrophy.

23. The method of claim 22, wherein the muscular dystrophy is Limb Girdle Muscular Dystrophy type 2C (LGMD2C).

24. The method of claim 20, wherein the antisense polynucleotide induces skipping of exon 4 (SEQ ID NO: 1), exon 5 (SEQ ID NO: 2), exon 6 (SEQ ID NO: 3), and exon 7 (SEQ ID NO: 4) of the gamma sarcoglycan RNA.

25. The method of claim 20, further comprising delivering to the cell an additional antisense polynucleotide that specifically hybridizes to an exon of a gamma sarcoglycan RNA.

26. The method of claim 20, wherein the delivering is oral or parenteral.

27. The method of claim 26, wherein the parenteral delivering is intravenous, intra-arterial, subcutaneous, intraperitoneal, or intramuscular.

28. The method of claim 27, wherein the delivering is by injection.

29. The method of claim 27, wherein the delivering is by infusion.

* * * * *

UNITED STATES PATENT AND TRADEMARK OFFICE
CERTIFICATE OF CORRECTION

PATENT NO.        : 9,499,817 B2
APPLICATION NO.   : 14/426348
DATED             : November 22, 2016
INVENTOR(S)       : Elizabeth McNally Page 1 of 1

It is certified that error appears in the above-identified patent and that said Letters Patent is hereby corrected as shown below:

On the Title Page

Item (57), Line 5, "aspect the" should be -- aspect of the --.

Signed and Sealed this
Ninth Day of May, 2017

Michelle K. Lee
*Director of the United States Patent and Trademark Office*